(12) United States Patent
Saliman et al.

(10) Patent No.: US 8,888,848 B2
(45) Date of Patent: *Nov. 18, 2014

(54) IMPLANT AND METHOD FOR REPAIR OF THE ANTERIOR CRUCIATE LIGAMENT

(71) Applicant: Ceterix Orthopaedics, Inc., Menlo Park, CA (US)

(72) Inventors: Justin D. Saliman, Los Angeles, CA (US); Mark S. Colella, Los Altos, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/893,209

(22) Filed: May 13, 2013

(65) Prior Publication Data

US 2013/0253647 A1 Sep. 26, 2013

Related U.S. Application Data

(63) Continuation of application No. 13/347,184, filed on Jan. 10, 2012, now Pat. No. 8,500,809.

(60) Provisional application No. 61/431,293, filed on Jan. 10, 2011.

(51) Int. Cl.
*A61F 2/08* (2006.01)
*A61B 17/04* (2006.01)

(52) U.S. Cl.
CPC ............ *A61F 2/08* (2013.01); *A61F 2/0811* (2013.01); *A61F 2002/0858* (2013.01); *A61B*

(Continued)

(58) Field of Classification Search
CPC ....... A61F 2/08; A61F 2/0811; A61F 2/0805; A61F 2002/0841; A61F 2002/0847; A61F 2002/088; A61F 2002/08478

USPC ............. 623/13.11–13.2; 606/232, 300, 301, 606/321

See application file for complete search history.

(56) References Cited

U.S. PATENT DOCUMENTS

| | | |
|---|---|---|
| 1,037,864 A | 9/1912 | Carlson et al. |
| 2,738,790 A | 3/1956 | Todt, Sr. et al. |

(Continued)

FOREIGN PATENT DOCUMENTS

| | | |
|---|---|---|
| EP | 0647431 A2 | 4/1995 |
| JP | 3032847 U | 3/1991 |

(Continued)

OTHER PUBLICATIONS

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

(Continued)

*Primary Examiner* — Christopher D Prone
(74) *Attorney, Agent, or Firm* — Shay Glenn LLP

(57) ABSTRACT

Described herein are methods and devices for use in repair of a patient's anterior cruciate ligament (ACL). These methods (and devices for performing them) allow the repair, rather than merely replacement, of the ACL. For example, described herein are anchoring devices that may be inserted into a bone and may anchor a scaffolding/support (e.g., graft) material within the bone so that the torn or damaged end of the ACL may be secured to the scaffolding/support material within the femoral notch. These anchoring devices and method of using them are particularly well suited for use with the continuous suture passers described herein, since these suture passers may allow access to previously inaccessible regions of the knee (or other body regions).

20 Claims, 31 Drawing Sheets

(52) U.S. Cl.
CPC .............. *2017/0412* (2013.01); *A61B 17/0401* (2013.01); *A61B 17/0485* (2013.01); *A61B 2017/0414* (2013.01); *A61F 2002/0882* (2013.01); *A61F 2002/0841* (2013.01); *A61B 2017/044* (2013.01); *A61B 2017/0445* (2013.01); *A61B 2017/045* (2013.01); *A61F 2/0805* (2013.01)
USPC .................................... 623/13.12; 623/13.11

(56) References Cited

U.S. PATENT DOCUMENTS

| | | |
|---|---|---|
| 2,748,773 A | 6/1956 | Vacheresse, Jr. |
| 3,470,875 A | 10/1969 | Johnson |
| 3,580,256 A | 5/1971 | Wilkinson et al. |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,112,344 A | 5/1992 | Petros |
| 5,129,912 A | 7/1992 | Noda et al. |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,532 A | 4/1995 | Loew et al. |
| 5,431,666 A | 7/1995 | Sauer et al. |
| 5,437,681 A | 8/1995 | Meade et al. |
| 5,454,823 A | 10/1995 | Richardson et al. |
| 5,454,834 A | 10/1995 | Boebel et al. |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,616,131 A | 4/1997 | Sauer et al. |
| 5,618,290 A | 4/1997 | Toy et al. |
| 5,626,588 A | 5/1997 | Sauer et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,800,445 A | 9/1998 | Ratcliff et al. |
| 5,814,054 A | 9/1998 | Kortenbach et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,159,224 A | 12/2000 | Yoon |
| 6,190,396 B1 | 2/2001 | Whitin et al. |
| 6,221,085 B1 | 4/2001 | Djurovic |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |

(56) References Cited

U.S. PATENT DOCUMENTS

| | | |
|---|---|---|
| 6,936,054 B2 | 8/2005 | Chu |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,394,112 B2 | 3/2013 | Nason |
| 8,449,533 B2 | 5/2013 | Saliman et al. |
| 8,465,505 B2 | 6/2013 | Murillo et al. |
| 8,500,809 B2 | 8/2013 | Saliman |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0282098 A1 | 12/2006 | Shelton et al. |
| 2007/0032799 A1 | 2/2007 | Pantages et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097489 A1 | 4/2008 | Goldfarb et al. |
| 2008/0140091 A1 | 6/2008 | DeDeyne et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0294256 A1 | 11/2008 | Hagan et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105751 A1 | 4/2009 | Zentgraf |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0306684 A1 | 12/2009 | Stone et al. |
| 2009/0306776 A1* | 12/2009 | Murray ..................... 623/13.12 |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2010/0331863 A2 | 12/2010 | Saliman |
| 2011/0028998 A1 | 2/2011 | Adams et al. |
| 2011/0060350 A1 | 3/2011 | Powers et al. |
| 2011/0087246 A1 | 4/2011 | Saliman et al. |
| 2011/0112555 A1 | 5/2011 | Overes et al. |
| 2011/0112556 A1 | 5/2011 | Saliman |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0218557 A1 | 9/2011 | Saliman |
| 2011/0251626 A1 | 10/2011 | Wyman et al. |
| 2011/0270280 A1 | 11/2011 | Saliman |
| 2012/0239062 A1 | 9/2012 | Saliman et al. |
| 2012/0283750 A1 | 11/2012 | Saliman et al. |
| 2012/0283753 A1 | 11/2012 | Saliman et al. |
| 2012/0303046 A1 | 11/2012 | Stone et al. |
| 2013/0072948 A1 | 3/2013 | States, III et al. |

FOREIGN PATENT DOCUMENTS

| | | |
|---|---|---|
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO 02/07607 A1 | 1/2002 |
| WO | WO 03/077771 A1 | 9/2003 |
| WO | WO 2006/001040 A1 | 1/2006 |
| WO | WO 2010/141695 A1 | 12/2010 |

OTHER PUBLICATIONS

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

(56) References Cited

OTHER PUBLICATIONS

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

Duerig, T. et al., "An overview of nitinol medical applications" Materials Science and Engineering A273-275, May 1999.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Strobel; Manual of Arthroscopic Surgery (1st Edition); Springer Verlag, Hiedelberg © 2002; pp. 127-129; Dec. 15, 2001.

USS SportsMedicine ArthoSewTM Single Use Automated Suturing Device with 8.6 mm ArthroPort Cannula Set, Instructions for Use, <http:www.uss-sportsmed.com/imageServer.aspx?contentID.5020&contenttype=application/pdf> accessed Apr. 25, 2007, 2 pages.

USS SportsMedicine ArthoSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

Hirotsuka et al.; U.S. Appl. No. 13/758,994 entitled "Pre-Tied Surgical Knots for Use With Suture Passers,", filed Feb. 4, 2013.

McCutcheon et al.; U.S. Appl. No. 13/759,000 entitled "Methods and Devices for Preventing Tissue Bridging While Suturing,", filed Feb. 4, 2013.

Saliman, J.; U.S. Appl. No. 13/759,006 entitled "Suture Passers,", filed Feb. 4, 2013.

Hendricksen et al.; U.S. Appl. No. 13/844,252 entitled "Suture passers and methods of passing suture,", filed Mar. 15, 2013.

Saliman et al.; U.S. Appl. No. 13/873,841 entitled "Devices, systems and methods for meniscus repair,", filed Apr. 30, 2013.

Murillo et al.; U.S. Appl. No. 13/893,154 entitled "Suture passer devices and methods,", filed May 13, 2013.

\* cited by examiner

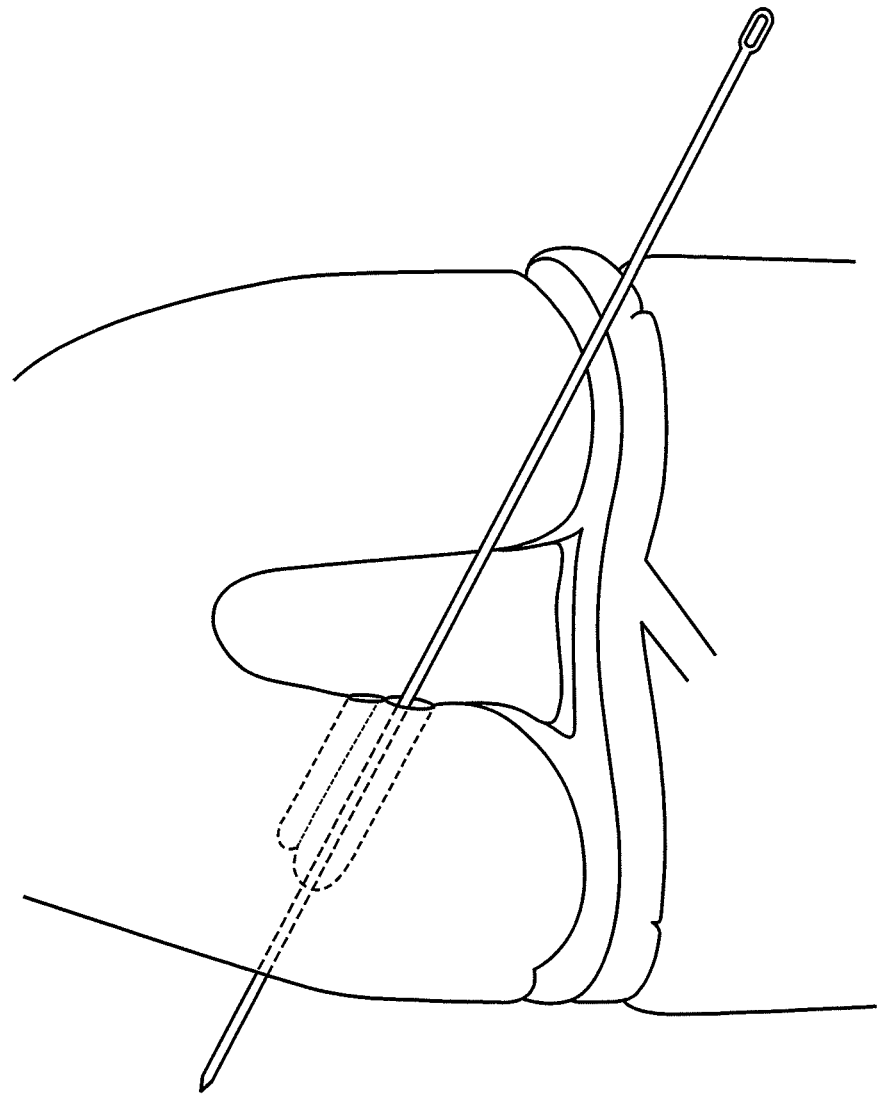
FIG. 3F
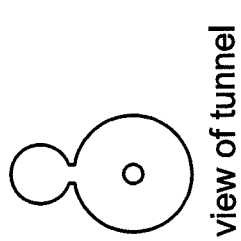
Axial view of tunnel
FIG. 3F1

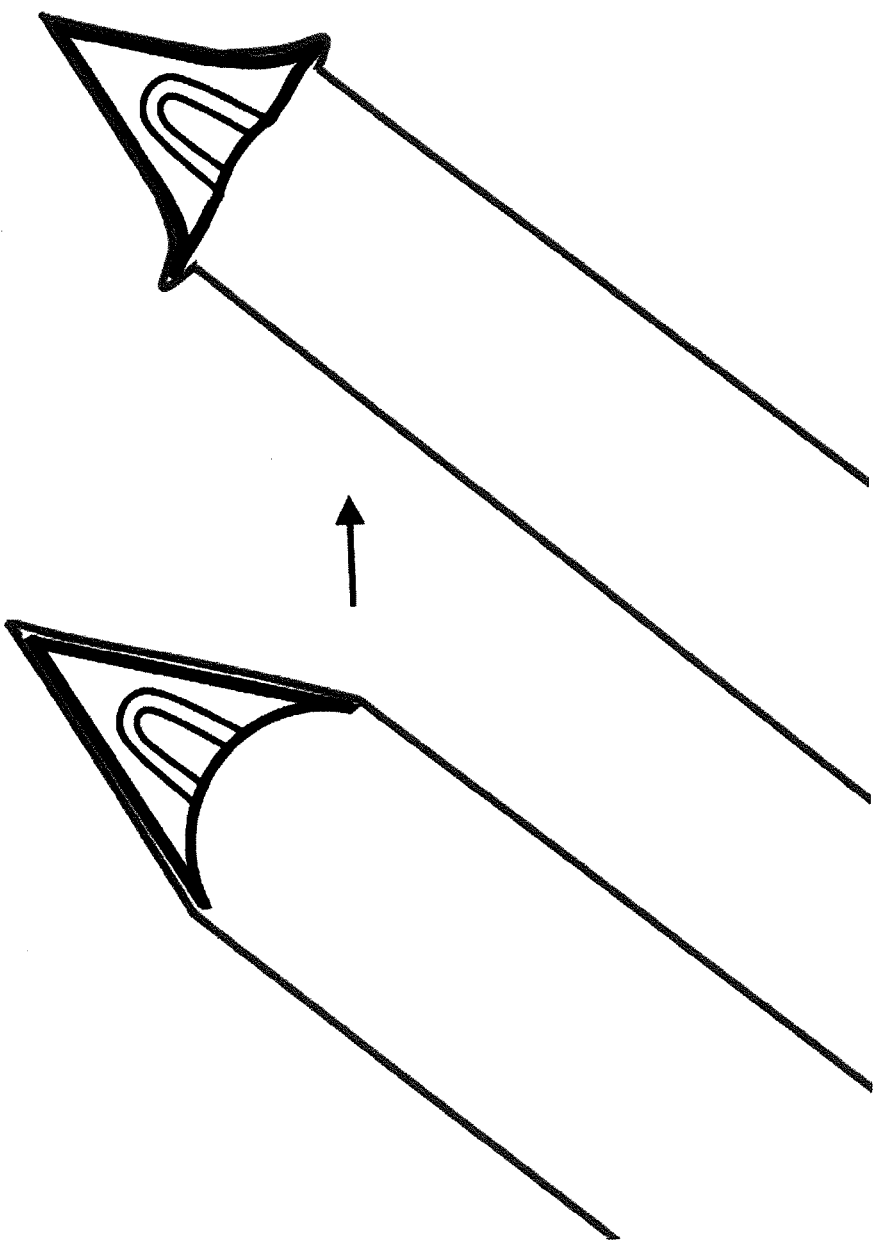

IMPLANT AND METHOD FOR REPAIR OF THE ANTERIOR CRUCIATE LIGAMENT

CROSS REFERENCE TO RELATED APPLICATIONS

This patent application is a continuation of U.S. patent application Ser. No. 13/347,184, filed on Jan. 10, 2012, titled "IMPLANT AND METHOD FOR REPAIR OF THE ANTERIOR CRUCIATE LIGAMENT," Publication No. US-2012-0179254-A1, now U.S. Pat. No. 8,500,809, which claims priority to U.S. Provisional Patent Application No. 61/431,293, filed on Jan. 10, 2011, and titled "IMPLANT AND METHOD FOR REPAIR OF THE ANTERIOR CRUCIATE LIGAMENT," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

In particular, the following patent applications are herein incorporated by reference in their entirety: U.S. patent application Ser. No. 11/773,388, filed Jul. 3, 2007, titled "METHODS AND DEVICES FOR CONTINUOUS SUTURE PASSING", Publication No. US-2009-0012538-A1; U.S. patent application Ser. No. 12/291,159, filed Nov. 5, 2008, titled "SUTURE PASSING INSTRUMENT AND METHOD", Publication No. US-2010-0331863-A2; U.S. patent application Ser. No. 12/620,029, filed Nov. 17, 2009, titled "METHODS OF SUTURING AND REPAIRING TISSUE USING A CONTINUOUS SUTURE PASSER DEVICE", Publication No. US-2010-0130990-A1; and U.S. patent application Ser. No. 12/942,803, filed Nov. 9, 2010, titled "DEVICES, SYSTEMS AND METHODS FOR MENISCUS REPAIR", Publication No. US-2011-0112556-A1.

FIELD

This invention relates to devices, systems and methods for repair of the anterior cruciate ligament (ACL).

BACKGROUND

Tears to the anterior cruciate ligament (ACL) are painful and often debilitating. Surgery for ACL injuries typically involves reconstructing the ACL using a graft material to replace the torn ACL. For example, ACL reconstruction surgery typically uses a graft to replace or support the torn ligament. The most common grafts are autografts from the patient (e.g., from a tendon of the kneecap or one of the hamstring tendons), though donor allograft tissue may also be used, as well as synthetic graft material. Although ACL reconstruction surgery is often referred to as ACL "repair" surgery, the current standard of care for ACL tears is to replace the torn ligament with a graft, rather than attempting to sew the torn ACL together. Merely sewing together the torn ACL has proven ineffective.

In general, ACL surgery may be performed by making small incisions in the knee and inserting instruments for surgery through these incisions (arthroscopic surgery) or by cutting a large incision in the knee (open surgery). During arthroscopic ACL reconstruction, the surgeon may make several small incisions around the knee. Sterile saline solution is pumped into the knee through one incision to expand it and to wash blood from the area. This allows the doctor to see the knee structures more clearly. The surgeon then inserts an arthroscope into one of the other incisions with a camera at the end of the arthroscope that transmits images of the internal region. Surgical drills may be inserted through other small incisions to drill small holes into the upper and lower leg bones where these bones come close together at the knee joint. The holes form tunnels through which the graft will be anchored. The surgeon may take an autograft at this point. The graft may also be taken from a deceased donor (allograft). The graft may then be pulled through the two tunnels that were drilled in the upper and lower leg bones. The surgeon may secure the graft with screws or staples and close the incisions with stitches or tape.

Unfortunately, replacing the ACL with a graft material, which requires anchoring both ends of the graft material to bone, has proven technically difficult, resulting in a long surgical time, and may ultimately require a long recovery time. Replacement of native ACL material with graft material typically leads to the loss of native ACL proprioceptive fibers, and results in an alteration of the native ACL tibial footprint geometry. In some cases, removing autograft material from the patient may result in donor site morbidity, while donor allograft material presents an increase risk of HIV and Hepatitis C transmission.

Thus, it would be desirable to provide devices, systems and methods for repair of the ACL that do not require the replacement of the ACL and the formation of multiple anchoring sites. The systems, devices and methods for repair of the ACL described herein may address these concerns.

SUMMARY OF THE DISCLOSURE

The present invention relates to systems, devices and methods for repair of ACL using an anchor for use with a graft material that may be sutured directly onto the torn ACL. In particular the systems and methods described herein may use a continuous suture passer such as those described in many of the applications previously incorporated by reference in their entirety, including at least: U.S. patent application Ser. No. 11/773,388, filed Jul. 3, 2007, titled "METHODS AND DEVICES FOR CONTINUOUS SUTURE PASSING", Publication No. US-2009-0012538-A1; U.S. patent application Ser. No. 12/291,159, filed Nov. 5, 2008, titled "SUTURE PASSING INSTRUMENT AND METHOD", US-2010-0331863-A2; U.S. patent application Ser. No. 12/620,029, filed Nov. 17, 2009, titled "METHODS OF SUTURING AND REPAIRING TISSUE USING A CONTINUOUS SUTURE PASSER DEVICE", US-2010-0130990-A1; and U.S. patent application Ser. No. 12/942,803, filed Nov. 9, 2010, titled "DEVICES, SYSTEMS AND METHODS FOR MENISCUS REPAIR", Publication No. US-2011-0112556-A1.

For example, described herein are methods for repairing a torn ACL within the femoral notch. In some variations, the methods include the steps of: anchoring a graft within the femoral notch; and suturing a torn end of the ACL to the graft within the femoral notch. In general, the step of anchoring the torn end of the ACL to the graft is performed percutaneously. The graft may be integral to (or preattached to) an anchor such as a knotless anchor. In some variations the torn end of the ACL is twice anchored within the femoral arch: both to a suture passed through and/or around the torn end of the ACL, and then to a graft that is anchored within the ACL. The connection to the graft may be made second, so that it may reinforce the suture which can be secured within the ACL to the same (or in some variations a different) bone anchor.

For example, in some variations, the step of anchoring a graft comprises securing an anchor to which a graft has been coupled within the femur so that a proximal end of the graft extends from the femur. For example, anchoring a graft may comprise driving a guidewire through the femur and drilling an opening to hold a graft anchor; and securing an anchor coupled to a graft within the opening over the guidewire.

The anchor may be secured by screwing the anchor into the opening (e.g., the tunnel drilled through a region of the femoral notch).

In some variations, the method includes securing the torn end of the ACL to a suture and pulling the suture through the femur to position the torn end of the ACL adjacent to the graft. The step of suturing the torn end of the ACL may comprise passing a suture through the graft and the ACL multiple times, e.g., with a suture passer that is adapted for use within the narrow confines of the tissue. For example, the step of suturing the torn end of the ACL may comprise passing a suture through the graft and the ACL multiple times with a continuous suture passer without removing the suture passer from the tissue.

In some variations the method further comprises securing the torn end of the ACL to a suture and pulling the suture through the femur to anatomically tension the ACL adjacent to the graft.

Also described herein are methods for repairing a torn ACL within the femoral notch, the method comprising: anchoring a graft within the femoral notch; positioning a torn end of the ACL adjacent to the graft; and percutaneously suturing the torn end of the ACL to the graft within the femoral notch.

In some variations, the step of positioning comprises securing a suture to the torn end of the ACL. For example, pulling the suture through a tunnel in the femoral notch to position the torn end of the ACL adjacent to the graft. In some variations, the method includes the step of anchoring the torn end of the ACL to the femoral notch with a suture before percutaneously suturing the torn end of the ACL to the graft.

In any of the variations of methods described herein, the method may include forming (e.g., drilling) a tunnel through the femoral arch for anchoring the torn ACL. The step of anchoring the graft within the femoral notch may include anchoring the graft within a tunnel drilled through the femoral arch.

Also described herein are methods for repairing a torn ACL within the femoral notch, the method comprising: drilling a tunnel through a portion of the femoral notch; anchoring a graft within the tunnel through the femoral notch, wherein the graft extends from the tunnel; pulling a suture connected to a torn end of the ACL through the tunnel through the femoral arch to positioning the torn end of the ACL adjacent to the graft; anchoring the suture connected to the torn end of the ACL; and percutaneously suturing the torn end of the ACL to the graft within the femoral notch.

BRIEF DESCRIPTION OF THE DRAWINGS

FIGS. 7A and 7B show another variation of a knotless ACL repair anchor.

DETAILED DESCRIPTION

Figure 1A:
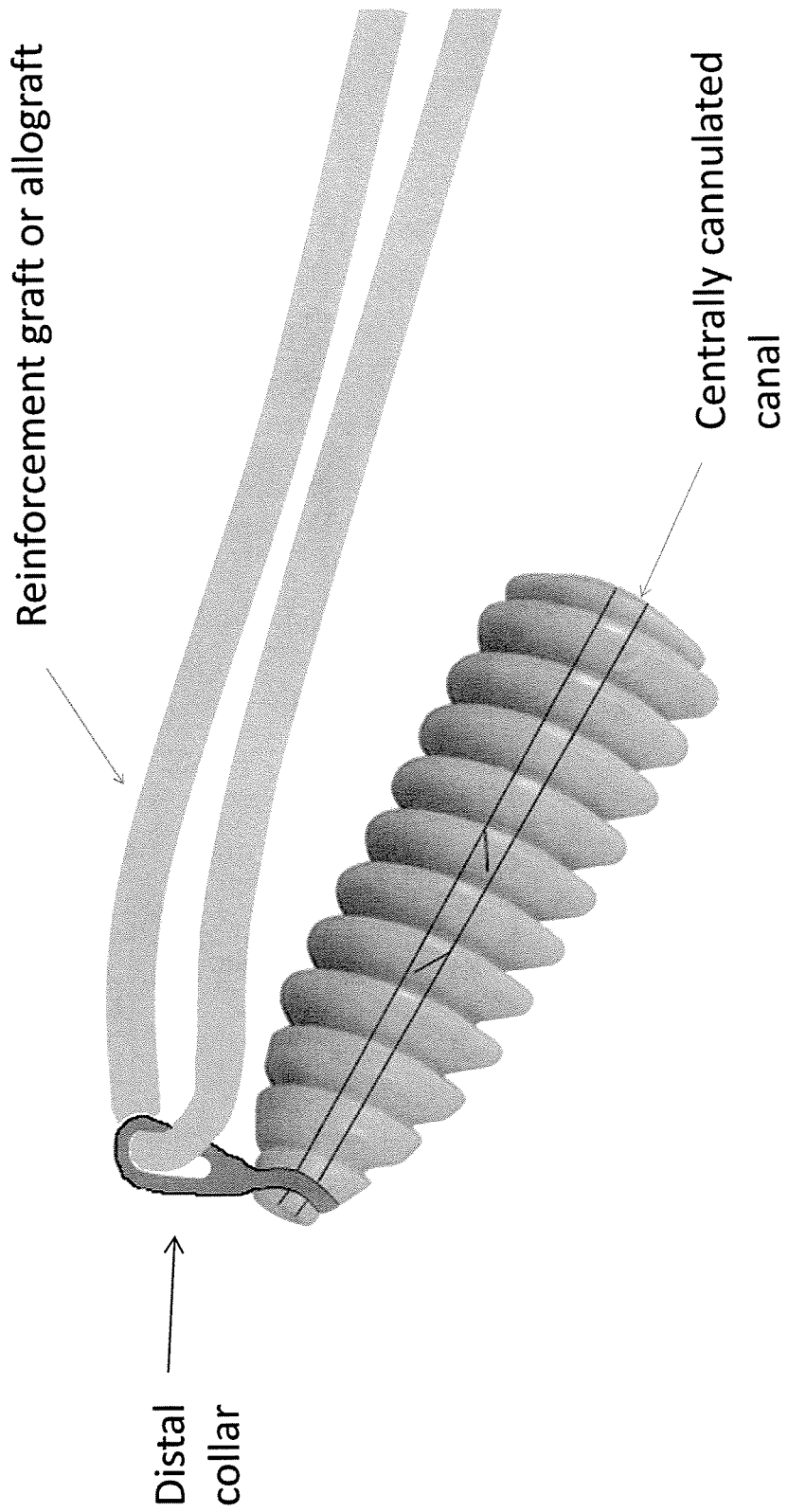
FIGS. 1A and 1B show one variation of a knotless ACL repair screw (anchor) as described herein.

In general, described herein are methods and devices for use in repair of a patient's anterior cruciate ligament (ACL). These methods (and devices for performing them) allow the repair, rather than merely replacement, of the ACL. It should be understood, however that the devices and systems described herein may also be used to replace an ACL. The anchoring devices described herein may be inserted into a bone and may hold a graft material within the bone so that the graft may also be attached to the torn or damaged ACL. The implanted anchoring device (which may also be referred to as an "implant" or "knotless graft anchor") may be particularly well suited for use with any of the continuous suture passers described herein, since these suture passers may allow access to previously inaccessible regions of the knee (or other body regions). For example, the methods described herein may include access into the notch region (e.g., the femoral notch) to anchor a graft in an optimal position, and to suture the graft to the damaged ACL while maintaining as much of the native ACL as possible. Previous methods of "repairing" (rather than replacing) the ACL have proven unsuccessful at least in part because this region was difficult or impossible to successfully access. Suturing in the notch region, without the benefit of the continuous suture passers described and incorporated by reference herein, has proven extremely difficult and time consuming, discouraging such surgical repairs.

Any appropriate graft material may be used with the systems, devices and methods described herein. For example, an ACL graft for use with the methods and devices described herein may include: synthetic grafts (e.g., Gore-Tex, Dacron, carbon fibers, and polypropylene braids, etc.), biologic (e.g., porcine, human or other) allografts, autografts, etc. The graft materials describe herein may provide support or scaffolding for repair of the torn ACL, since the ACL is left in place and sutured to the graft. Thus, in some variations the graft may be a sleeve or patch (e.g., a graft jacket, Restore patch, etc.) The graft may include a biologic material such as a growth-promoting material that may promote in-growth, visualization, or the like (e.g., growth factors, etc.).

In general, the devices described herein include a knotless ACL graft anchor, which may also be referred to as an ACL graft anchor, a one-way ACL graft anchor, a knotless ACL repair screw, or merely a "device". These ACL graft anchors may include a one-way path for passing (and therefore anchoring) a suture, as well as a coupling region for coupling to a graft material. The one-way path may be a central passage through the device. In general the one-way path forms a channel through the device and may include cams or other locking members that prevent a suture passing through the one-way path from pulling out the device. The one-way path may be referred to as the suture channel or path, since the suture may extend through (and be held within) the one-way path, although other elements (e.g., a guidewire, such as a beath pin, etc.) may also be passed through the channel. The one-way channel may extend from the proximal to the distal ends of the device, which may advantageously allow the ACL graft anchor to be easily implanted and positioned, and may anchor the suture (e.g., connected to an ACL) at or within a bone region of the femoral notch. For example, the suture may be drawn through the implant to pull the distal end portion of a torn ACL towards (and to or into) the proximal end of the ACL graft anchor. The anterior end of the implant is typically the end that is not completely inserted into the bone, or that faces away from the bone.

As mentioned above, the anchors described herein allow both securing (e.g., suturing) of the torn ACL to the scaffold/support (e.g., graft) after the graft has been anchored into the bone, but also tensioning of the torn ACL by pulling and locking the position of a suture that has been secured to the torn end of the ACL. In particular, the anchor includes a one-way pathway that allows the suture connected to the torn end of the ACL to be pulled and held (locked) distally, to adjust the tension on the ACL as it is being positioned adjacent to the graft so that it can then be sutured to the graft. The one-way locking mechanism in the suture pathway through the anchor allows this tensioning. Thereafter, the reinforcing support of the graft (scaffolding) maintains the tension and position of the ACL for short-term repair and long-term healing. Thus, described herein are anchor devices that are configured to both pre-tension a torn ACL and to secure the tensioned ACL to the reinforcement graft anchored in the bone by the device. In general, these devices therefore include a one-way (locking) path for a suture to be drawn through the body of the anchor as well as a coupling region for a graft, or a graft that is already integrally part of the device.

The coupling region that may couple to a graft may be located as the distal end (e.g., the end to be inserted into the bone) of the device so that the graft will be anchored at one end in the bone. The coupling region may be positionable or rotatable around the circumference of the device. In some variations the coupling region is a loop or ring that is rotatably attached around the distal end region of the ACL anchor, which is also connected to a second loop or ring through which the graft (e.g., ACL graft) may pass and be secured. A coupling region may be referred to as a collar. Alternatively, the attachment region may include a suturing substrate (e.g. fabric) to which the graft may be coupled or connected. In some variations, the coupling region may include a passage through the device through which the graft may be passed. In some variations the coupling region is connected (or formed of) the distal end of the ACL anchor, which may be rotatable around the long axis of the ACL graft anchor.

Thus, in general, the ACL anchors described herein are configured to secure both an ACL graft (which is to be sutured to the ACL) and a suture that is also connected to the torn ACL.

The ACL anchors described herein may also be configured to secure within an opening drilled into the bone. For example, the sides may be self-tamping, ridged, expandable, or the like, to secure the anchor within the bone. The body of the anchor may also include one or more passages or opening into which bone may grow (or be encouraged to grow). In some variations the device includes lateral openings into which a cross-pin or other additional anchoring device may be inserted.

Figure 1B:
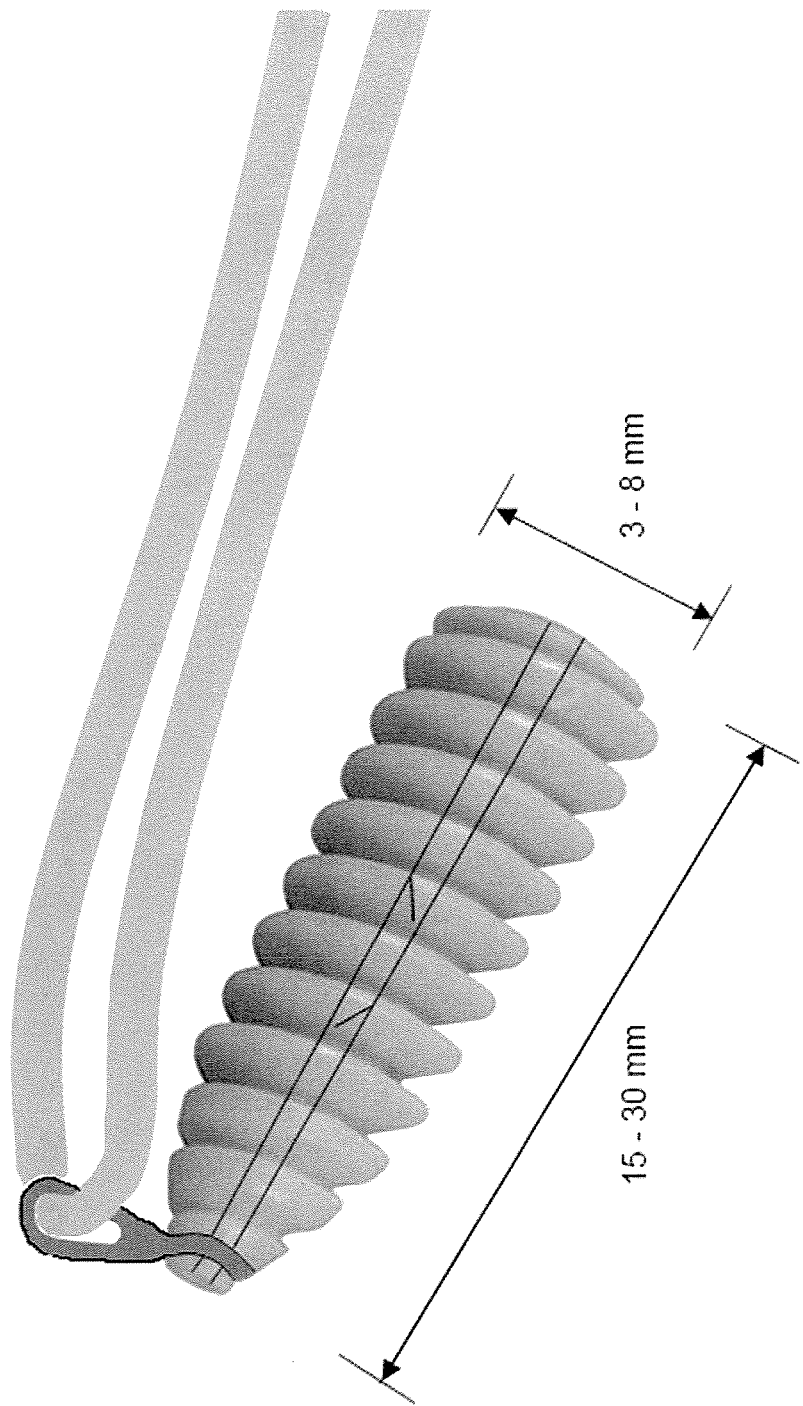

For example, FIGS. 1A and 1B show one variation of a knotless ACL repair screw. In this example the ACL graft anchor has a screw-shape body (e.g., a threaded body) that extend in a proximal-distal longitudinal direction. The distal end includes a distal collar for attachment to a graft material; the distal collar (coupling region) includes a loop through which the graft material may pass and be secured, and a collar region surrounding an opening at the distal end. Thus, the collar can rotate relative to the body of the device. This allows the threaded, screw-shaped body to be screwed (rotated) into position within the bone, while the graft at the distal end may remain in the same position (e.g., on one side of the body). In FIG. 1A, the distal collar can rotate freely with respect to the screw (body of the anchor), and has an eyelet through which any reinforcement graft or allograft can be inserted (e.g., a graft jacket, Restore Patch, tibialis anterior allograft, etc.).

The ACL repair screw (anchor) body in FIG. 1A may be made out of PEEK material. In this example, the outer body region is threaded for screwing into a channel made in the bone. The device includes a central channel that creates a one-way passage for a suture, and can thereby anchor a suture in position. For example, the central channel may include tabs that create a one-way pathway for a suture. In other variation the suture is allowed to pass only in one direction (e.g., towards the distal end of the implant) by tabs, clamps, cams, ball valves, check valves, or the like).

FIG. 1B shows the device of FIG. 1A with exemplary range of dimensions (e.g., length of approximately 15-20 mm, and width of approximately 3-8 mm). In some variations, a smaller diameter screw may be beneficial because a smaller diameter screw will allow more contact of the ligament to bone at the repair site.

Figure 6:
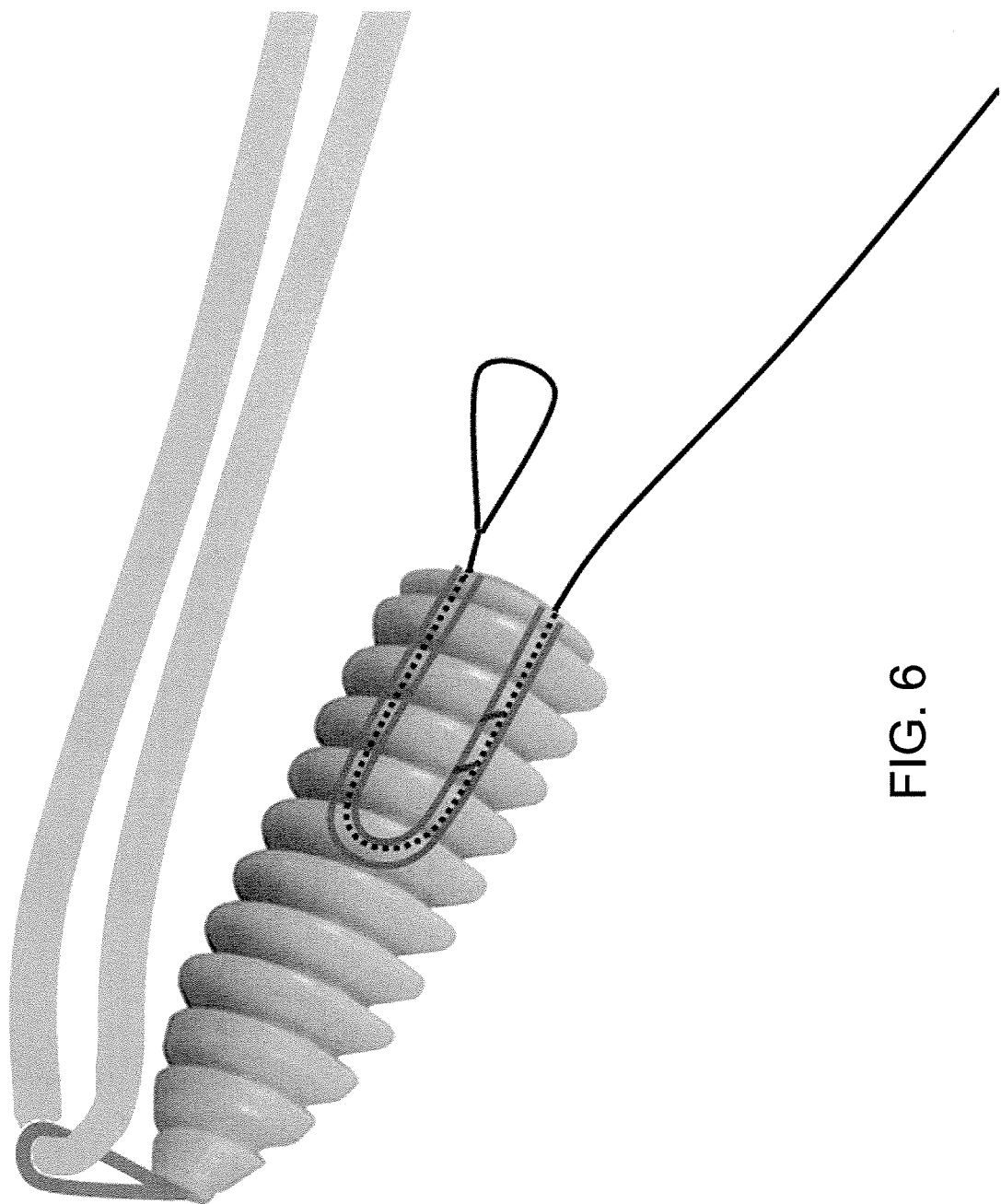
FIG. 6 shows another variation of a knotless ACL repair screw.

FIGS. 5 to 7B also illustrate alternative variations of anchors that may be used with the systems and methods described herein. For example, in FIG. 5, the anchor includes a central one-way path for a suture that is locked in place by a ball valve. In FIG. 6, the anchor does not include a passageway completely through the anchor, but instead has a passageway that passes both in and out of the anchor at the proximal end. The passageway may also be valved to allow only one-way travel through the device, as shown. In both FIG. 5 and FIG. 6, the embodiments shown include a suture forming a loop at the distal end, which may be connected to an ACL so that the ACL may be drawn towards and anchored into position relative to the anchor. FIGS. 4A to 4D, described in greater detail below, illustrate securing the end of an ACL to a suture so that it can be loaded into a knotless anchor.

FIGS. 7A and 7B illustrate another variation of an ACL anchor in which the anchor secured itself into position within a hole or opening in the bone. This design may allow for a smaller hole to be made in the bone (e.g., the bone forming the notch region). In this example, as shown in FIG. 7A, the implant (with a one-way passage) is inserted into a passage in the bone as shown. In this example, the scaffold material (e.g., graft) is not shown, but is included. Once in position, the anchor may be locked in place by expanding at least a region of the implant. For example, in FIG. 7B, the proximal end of the device expands outwards against the walls of the opening or passage in the bone, locking it in place, as shown. A suture (not shown) may be pulled through the one-way passage in the anchor, to draw the ACL towards the device, and potentially into the bone. The ACL may then be secured in position and so that in-growth can help anchor it in place. In some variations, the anchor includes a cam or camming mechanism that may create a one-way anchor within the channel for the suture.

As mentioned above, any appropriate suture passer may be used, particularly those described in: U.S. patent application Ser. No. 11/773,388, filed Jul. 3, 2007, titled "METHODS AND DEVICES FOR CONTINUOUS SUTURE PASSING", Publication No. US-2009-0012538-A1; U.S. patent application Ser. No. 12/291,159, filed Nov. 5, 2008, titled "SUTURE PASSING INSTRUMENT AND METHOD", Publication No. US-2010-0331863-A2; U.S. patent application Ser. No. 12/620,029, filed Nov. 17, 2009, titled "METHODS OF SUTURING AND REPAIRING TISSUE USING A CONTINUOUS SUTURE PASSER DEVICE", Publication No. US-2010-0130990-A1. For example, suture passers having a suture shuttle that is configured to clamp to the side of a curved tissue penetrator that can be extended and retracted to pass the suture shuttle (and any attached suture) back and forth between two open/closed jaws or arms are of particular interest. In this example, the suture shuttle may generally include a shuttle body that clamps to the tissue penetrator, and has an extension region ("leash") with a suture attachment region at the end. In this way the suture may be held slightly apart from the tissue penetrator, and not interact directly with the tissue penetrator.

Figure 8B:
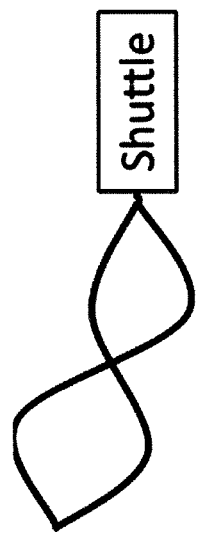
FIGS. 8A and 8B illustrate two variations of lead wires configured to extend from a suture shuttle for use with a continuous suture passer as described herein.
Figure 8A:

In some variations, the shuttle used for passing the suture by a continuous suture passer may be further adapted for use with the devices and methods described herein. For example, the shuttle may be configured to include a lead wire that allows a region of one or more loop to be cut free after the initial ACL suture is placed (because the central part of the suture may be passed to allow a loop to be formed, through which the proximal aspect of the suture ends can be inserted for a self-cinching pattern. See, for example, FIGS. 4A-4D. FIGS. 8A and 8B illustrate variations of suture shuttles including multiple (two in this example) loops extending from the body of the suture shuttle. The outer loop may be cut away, broken or otherwise opened to release a suture or loop of suture. The same suture shuttle may the then be used again without having to remove it from the tissue, and without having to draw one or both free ends of the suture out of the loop.

Figure 9B:
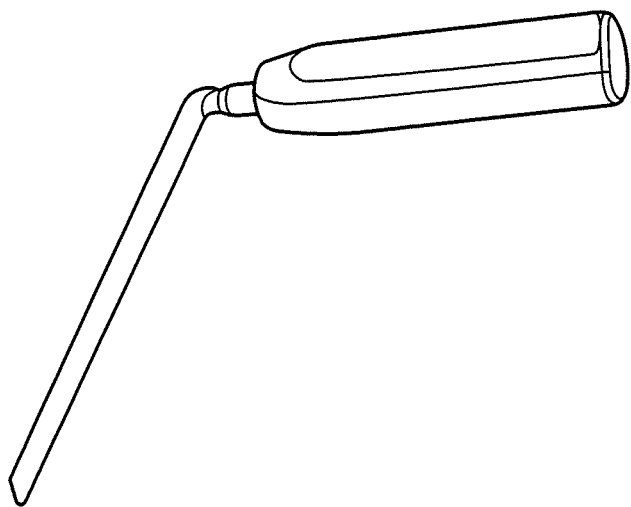
FIGS. 9A and 9B illustrate arthroscopic spatulas that may be used for knot typing and instrument insertion during any of the methods described herein.
Figure 9A:
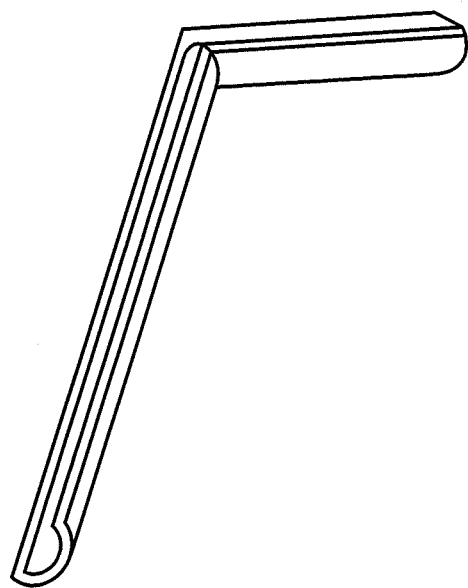

In any of the variations described herein, one or more arthroscopic devices may be used to help manipulate the tissue, in addition to the suture passers (or in place of the suture passers) described. For example, FIGS. 9A and 9B illustrate two variations of arthroscopic spatulas that may be used for knot typing and instrument insertion, as appropriate.

In general, any of the anchors described herein may be used as part of a system for repairing ACL. Such a system may also include a continuous suture passer and or suture material. In particular, continuous suture passers that are capable of passing a suture back and forth (e.g., by connection to a shuttle member) between two arms or jaws while the jaws are open around the tissue (e.g., ACL tissue), are of particular interest. Thus, the system may include the suture passer, one or more suture shuttles and one or more anchors as described herein. For example, the shuttles described may include those illustrated in FIG. 8A or 8B. In some variations, the systems also include a tool or tools for forming a hole or opening in bone of the notch into which the anchor may be positioned, and a guidewire, needle or pin for inserting the device and/or for threading a suture through the anchor. Additional manipulation tools, including those shown in FIGS. 9A and 9B, may also be included.

Methods of Repairing ACL

Also described herein are methods of repairing a torn ACL. These methods may generally include anchoring one end of a scaffold in the femoral notch, for example, by securing an anchor that holds one end of a flexible scaffold for attaching to the patient's ACL. The scaffold may be a graft, sleeve, patch, or the like. The anchoring may include anchoring a scaffold (e.g., graft) using an ACL graft anchor such as those described above. The scaffold may be secured by first driving a pin (e.g., beath pin) though the posterolateral femoral arch), drilling an opening into which the ACL graft anchor may sit. In some variations a second tunnel or passage for the graft, adjacent to the first, may also be formed. An ACL graft anchor with an attached ACL scaffold may then be secured into the opening formed through the femoral arch bone. In some variations a guidewire may be used to guide both the drill and/or the ACL graft anchor so that it can be positioned. Once the scaffold (e.g., graft) is anchored in the femoral arch, the torn end of the ACL, in variation in which the ACL has torn away, may be pulled towards the ACL anchor and scaffold and sutured to the scaffold while in the notch. For example, the end of the torn ACL may be sutured or connected to a suture and the suture drawn though the body of the suture anchor to pull the end of the ACL towards the anchor and the graft. The suture may hold the ACL in position so that it may be sutured (using a separate suture) to the graft material, thereby re-attaching the ACL to the femoral arch region. In some variations the end of the suture is passed through the anchor distally, along the one-way passage through the anchor, holding it in position.

For example, FIGS. 2A-2D illustrate one variation of a method for anchoring a scaffolding (e.g., an ACL graft) and also a method for positioning a torn ACL next to the anchor and graft so that it can be sutured to the graft. FIGS. 3A-3P show an example of a method for repairing an ACL, including steps for anchoring the scaffolding/support in the femoral notch and suturing the ACL to the scaffolding support while the end of the ACL is in the femoral notch.

Figure 2A:
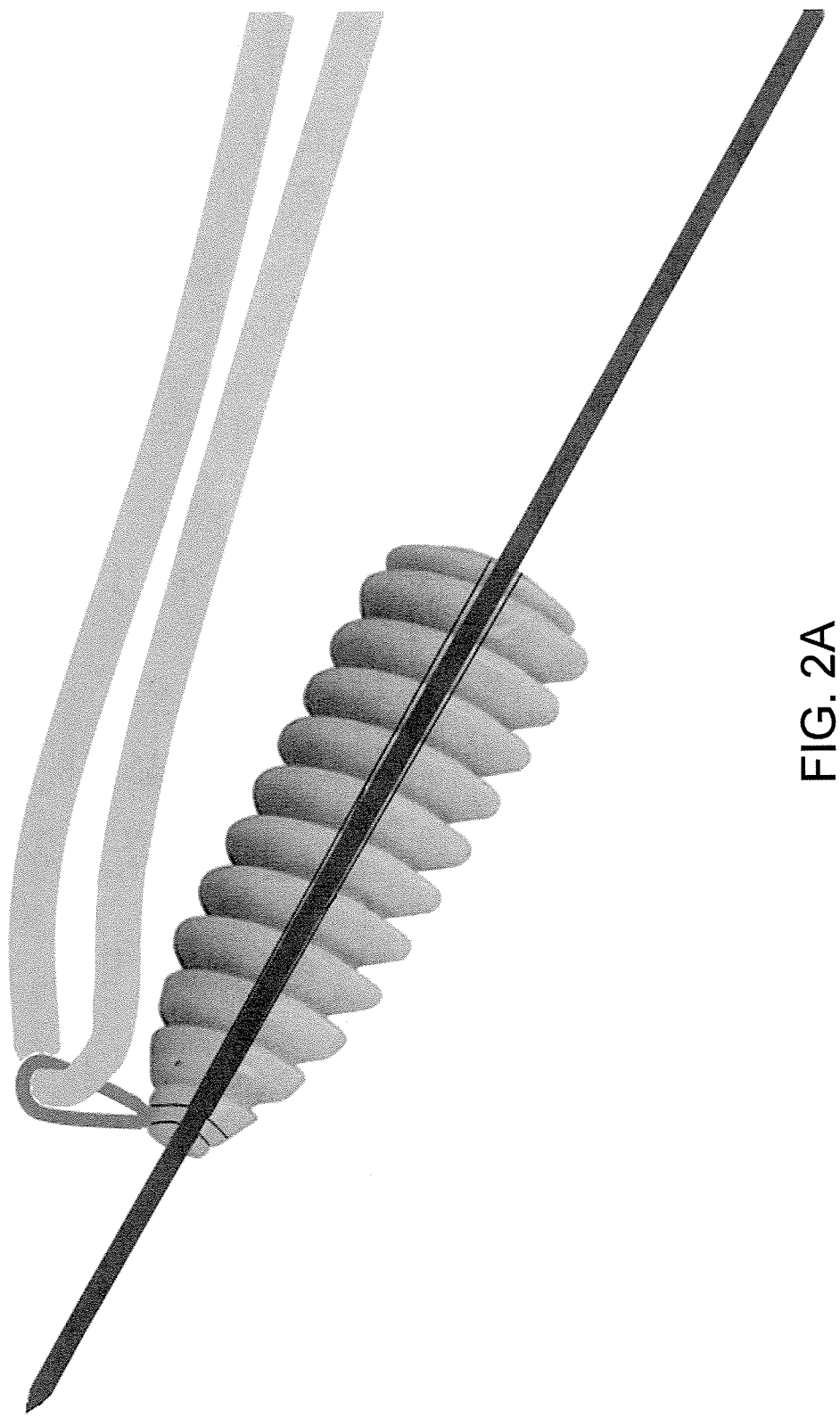
FIGS. 2A-2D illustrate one method of loading a suture into a knotless ACL repair screw such as the variation shown in FIGS. 1A-1B.
Figure 3A:
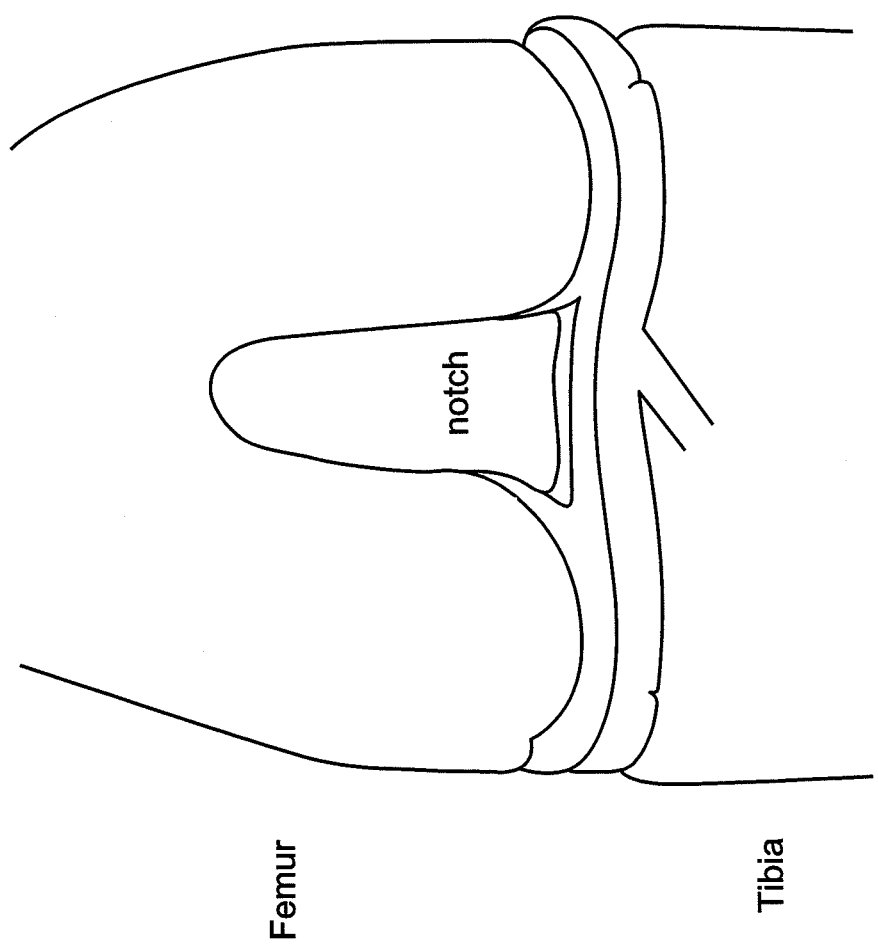
FIGS. 3A-3P illustrate one method of repairing an ACL using a knotless ACL repair screw.
Figure 3B:
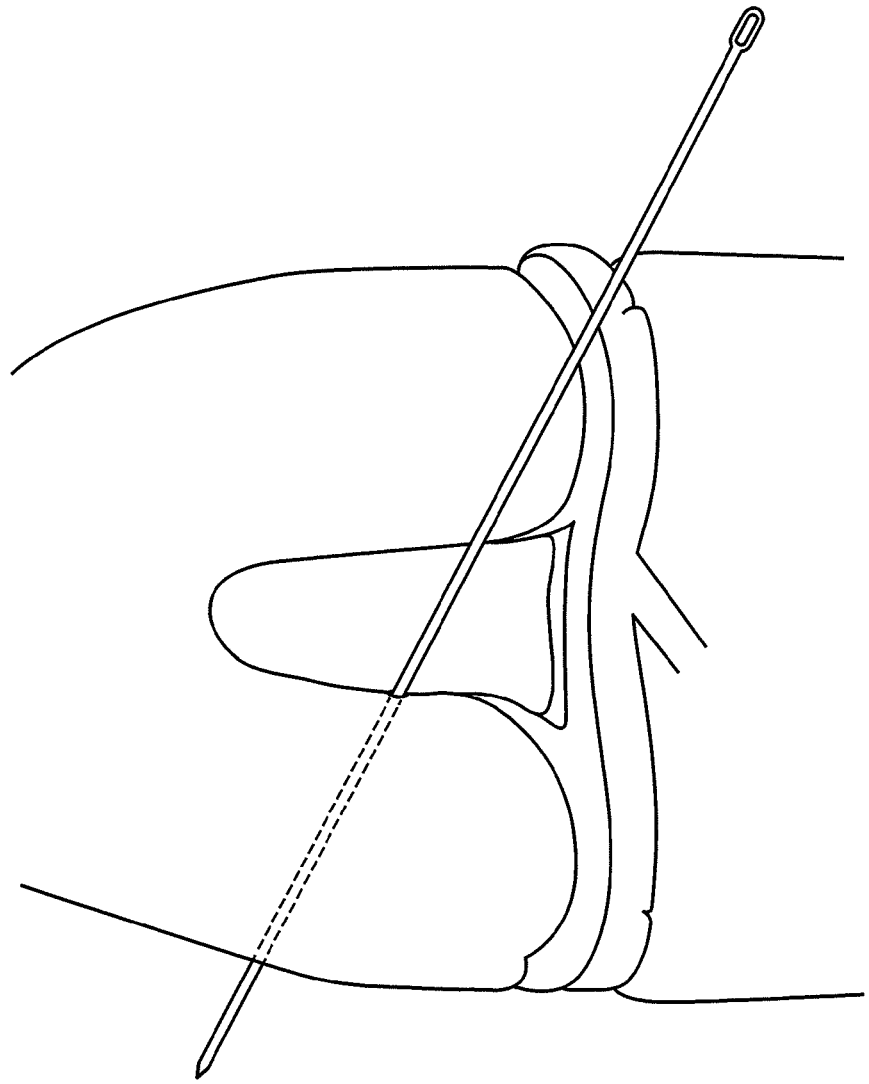
Figure 3C:
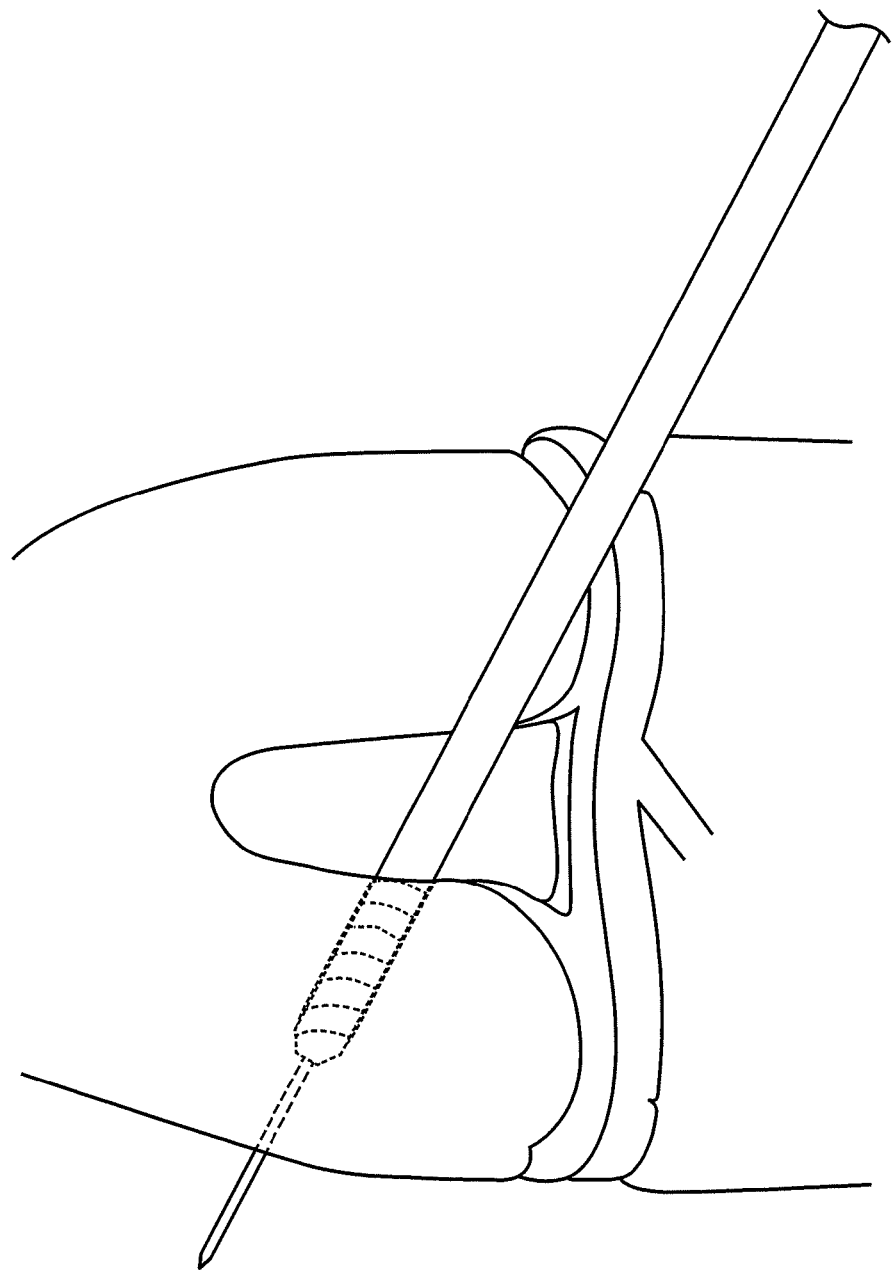
Figure 3D:
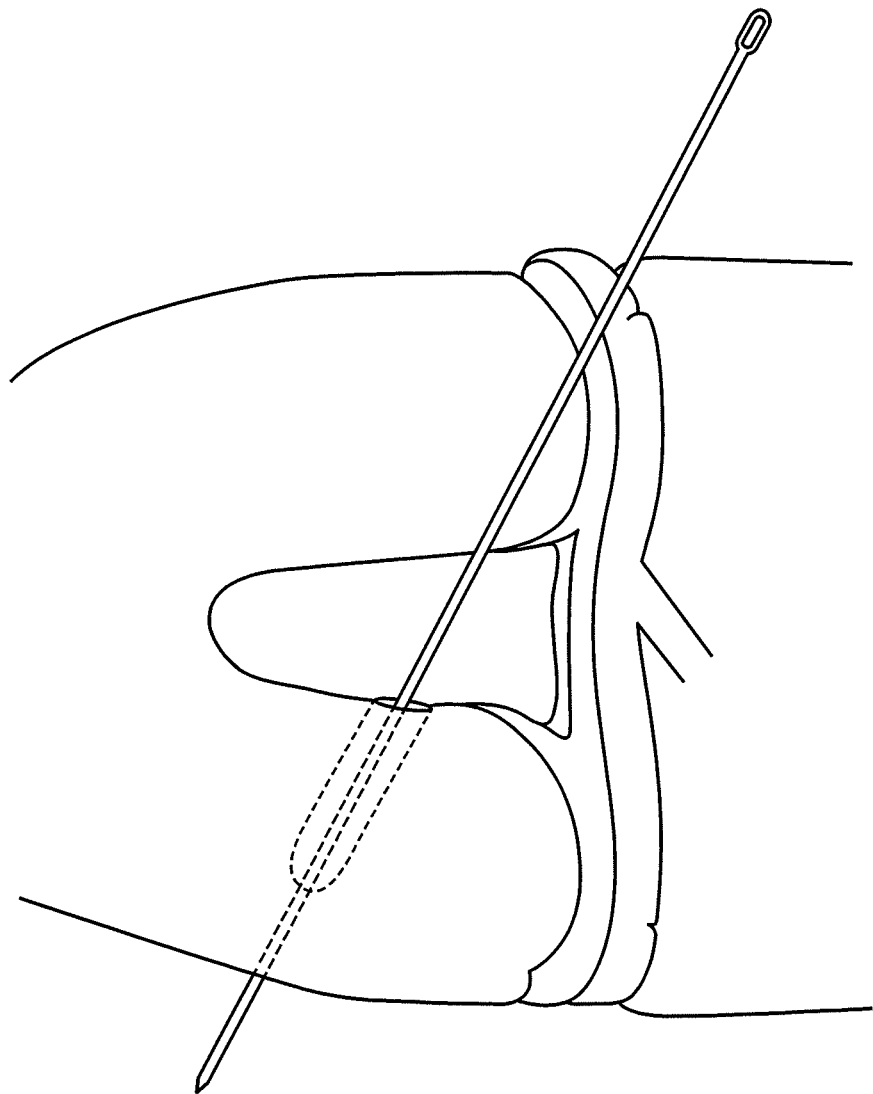
Figure 3E:
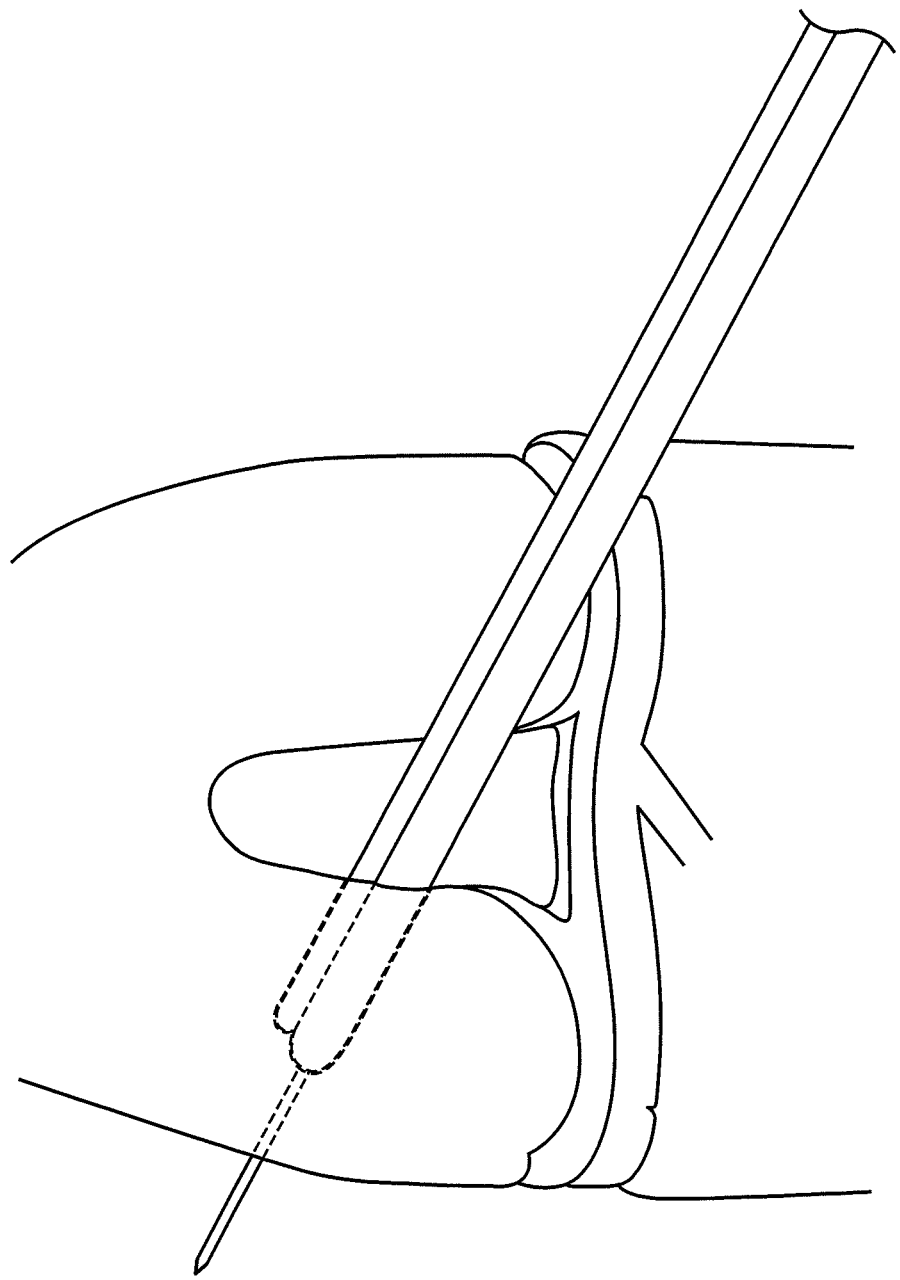

In FIG. 2A, the anchor, which in this embodiment is shown similar to the variation of FIGS. 1A and 1B as an ACL screw anchor, may be threaded over a guide wire. Any appropriate guidewire may be used, for example, a beath pin type of guidewire that is known to be used in ACL reconstruction. The guidewire is threaded through the central (one-way suture passage) of the anchor, and in this variation the guidewire may disable the one-way cams/tabs within the channel that prevent the suture from being pulled proximally when a suture is passed through the channel. For example, the one-way tabs may fold to allow passage over the pin/guidewire. As shown in FIGS. 3A-3P, the guidewire or pin may be used to place or position the anchor into a hole formed in the femoral notch, to place and thereby anchor the ACL graft.

Figure 2B:
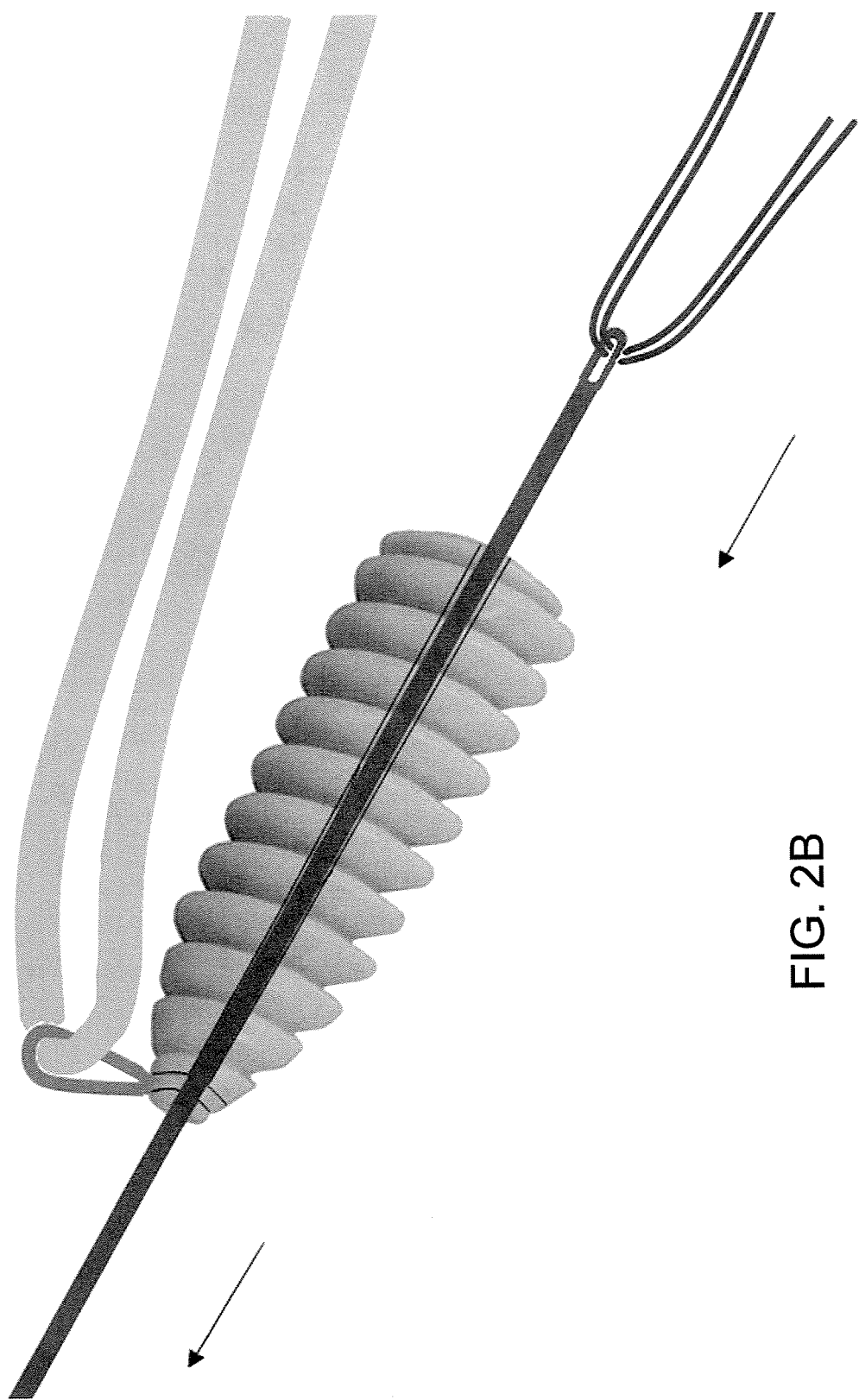
Figure 2C:
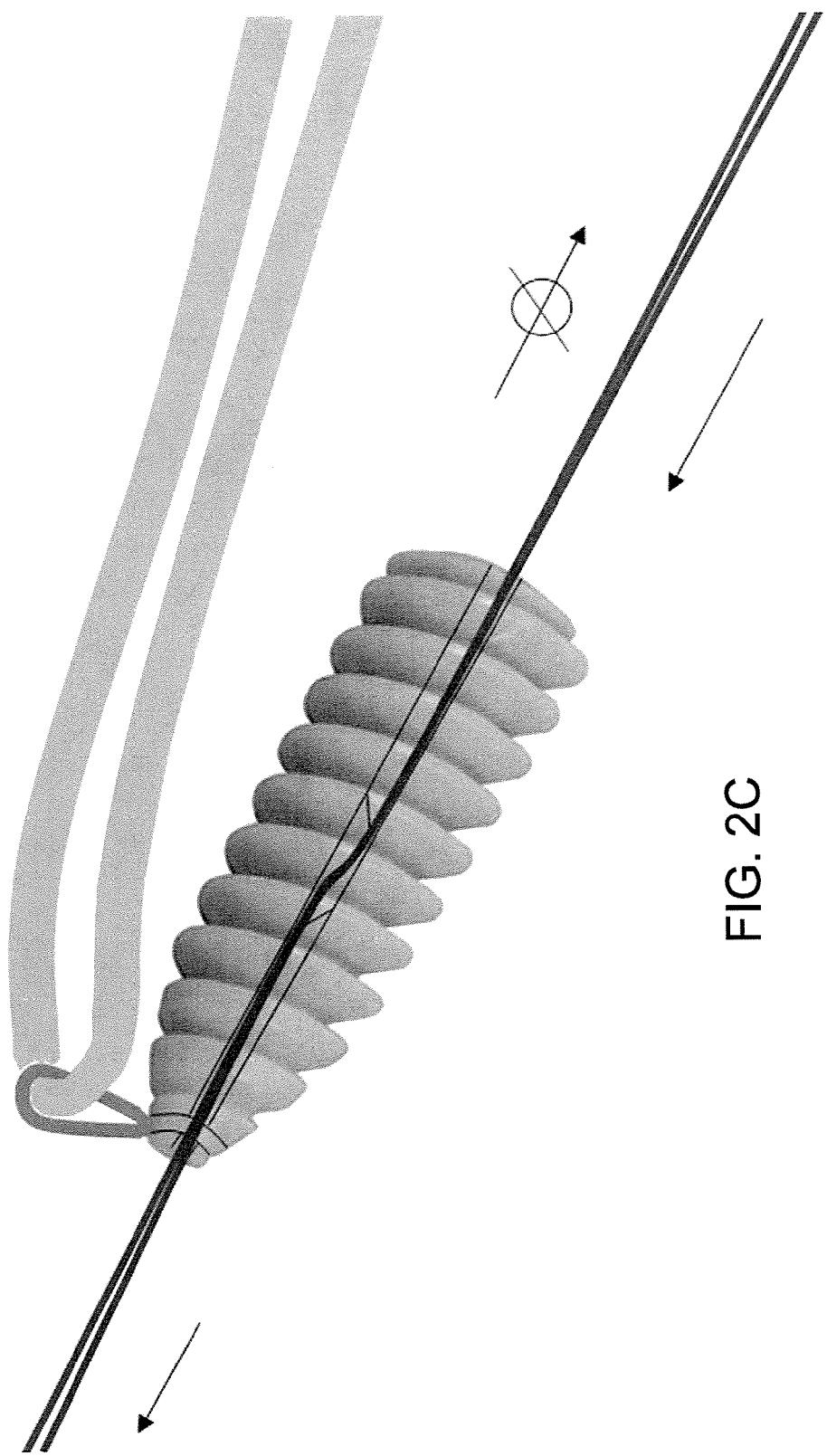
Figure 2D:
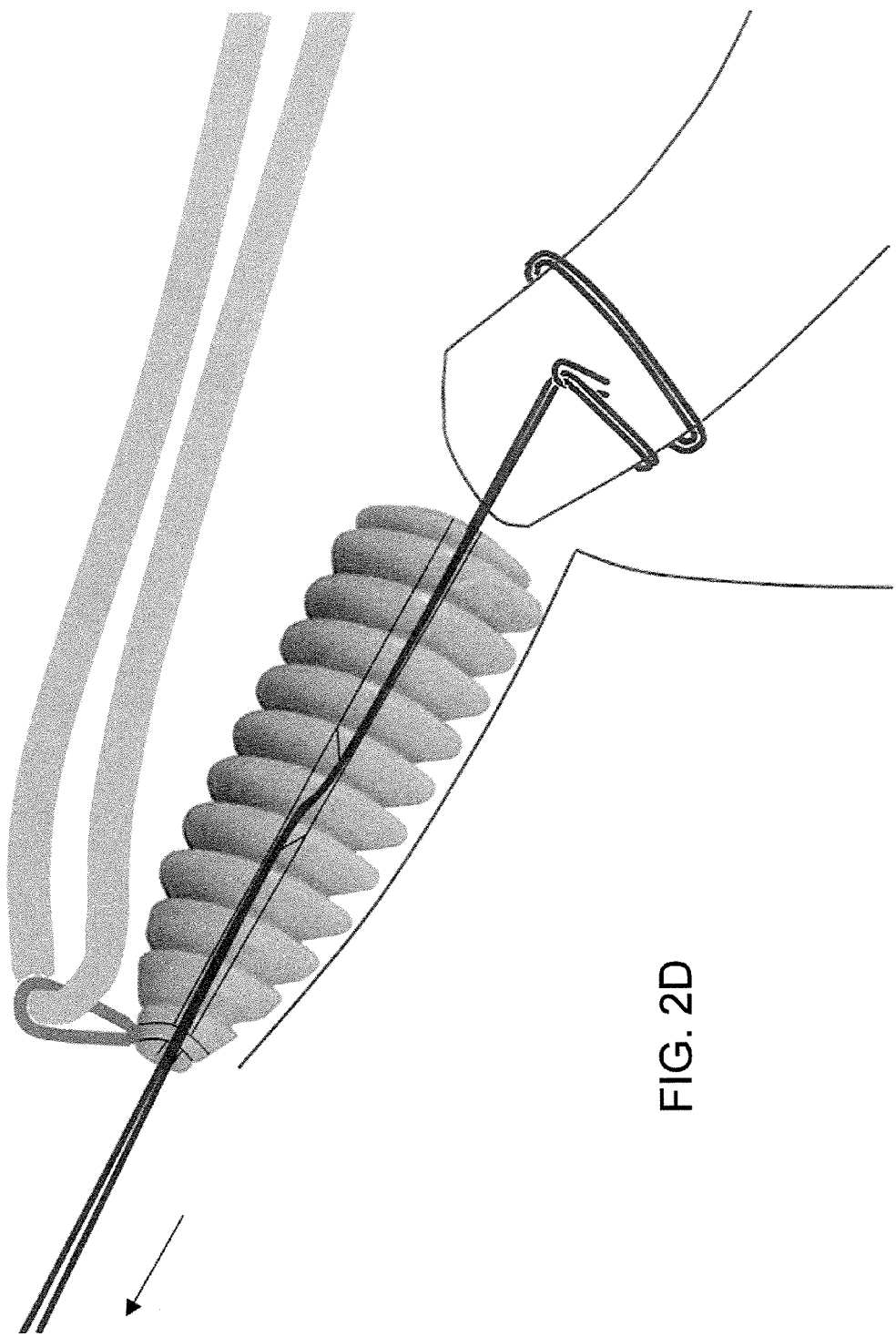

In FIG. 2B, sutures are loaded into the beath pin eyelet and the beath pin (guidewire) is pulled distally through the screw to load the sutures into the anchor, as shown. In this example, the anchor may already be positioned within the notch (not shown), and the sutures may already be secured to the end of the ACL. For example, in FIG. 2C, the sutures are loaded into the anchor, and pulling on the sutures to the left (through the anchor) pulls the ACL tissue toward the anchor base (the proximal end of the anchor) through the suture channel in the anchor, in a one-way, self tightening fashion. In this example, the suture channel includes cams or tabs that allow the suture to be pulled distally but not proximally, as indicated by the arrow. Eventually, as shown in FIG. 2D, the ACL to which the suture is attached will be pulled adjacent to the proximal end of the anchor (not drawn to scale, as the ACL will typically be much larger than the anchor). In some variations, the ACL may be pulled at least partially into the channel formed in the bone into which the anchor is placed. Once the ACL is pulled (via the suture) adjacent to the anchored scaffolding or graft, it may be sutured to the scaffolding (e.g., graft) using the continuous suture passer, while positioned in the femoral notch.

In one variation, the ACL is sutured to the anchor prior to implanting the anchor in the femoral notch, and the anchor with the end of the femoral notch is then positioned (e.g., by pulling the anchor using a guidewire and or the suture) into position, where it can be expanded or otherwise fixed into position.

FIGS. 3A-3P illustrate one method for repair of an ACL. In this example, the ACL has ruptured proximally within the femoral notch, and the procedure is performed within 3 weeks of the injury. FIG. 3A illustrates a portion of the patient's knee, showing the joint between the femur and the tibia, and in particular illustrating the femoral notch ("notch"). In FIG. 3B the notch is prepared by driving a beath pin into the posterolateral femoral notch, as shown. Alternatively, the region may be drilled or otherwise penetrated to form a narrow passage through femur head from the femoral notch. In this example, the beath pin is driven from within the notch and through the femur head region. Next, as shown in FIG. 2B, the pin is then over-drilled to form a cavity into which the anchor may be seated; the opening faces the notch. In this example, the cavity is drilled with a bit that is approximately one size smaller than the anchor (a screw-type anchor is illustrated here). For example if the outer diameter of the anchor is about 5-6 mm in diameter, the drill bit diameter may be about 4-5 mm. The depth of drilling may be slightly longer than the length of the anchor. For example, in this illustration the depth of drilling is approximately 25 mm, as shown in FIG. 3D.

In some variations, particularly those in which the scaffold (e.g., graft) attached to the distal tip of the anchor is positioned to the side of the anchor (as illustrated in FIG. 1A), a second cavity may be formed adjacent to the anchor cavity to allow room for the graft. This is shown in FIG. 3E. In this example, a dual barrel impacter is driven (e.g., malleted) along the guide wire (beath pin) to create a second, smaller tunnel just superior to the previously drilled hole. This is shown in FIGS. 3F and 3F1. The graft may fit into the adjacent tunnel without substantially weakening the attachment of the anchor.

Figure 3G:
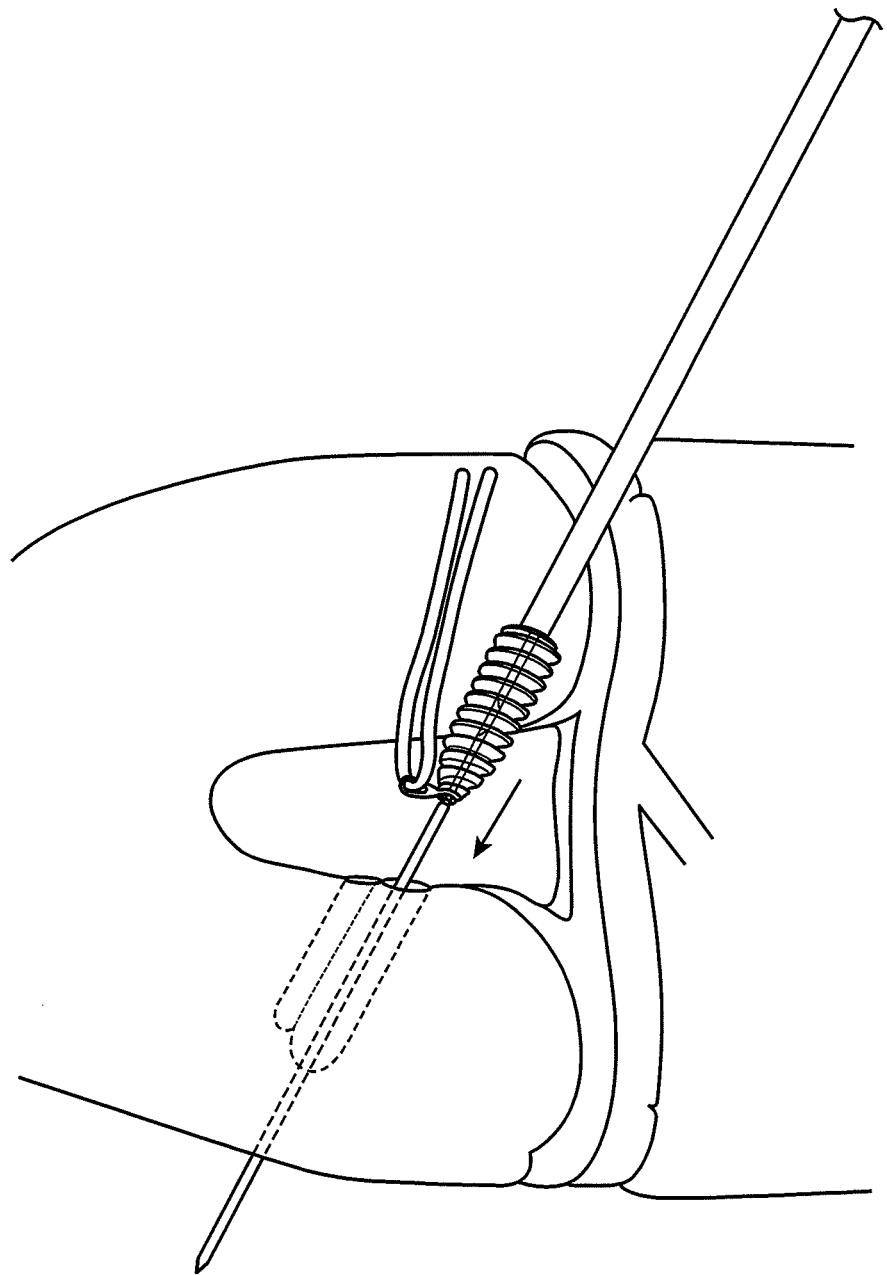
Figure 3H:
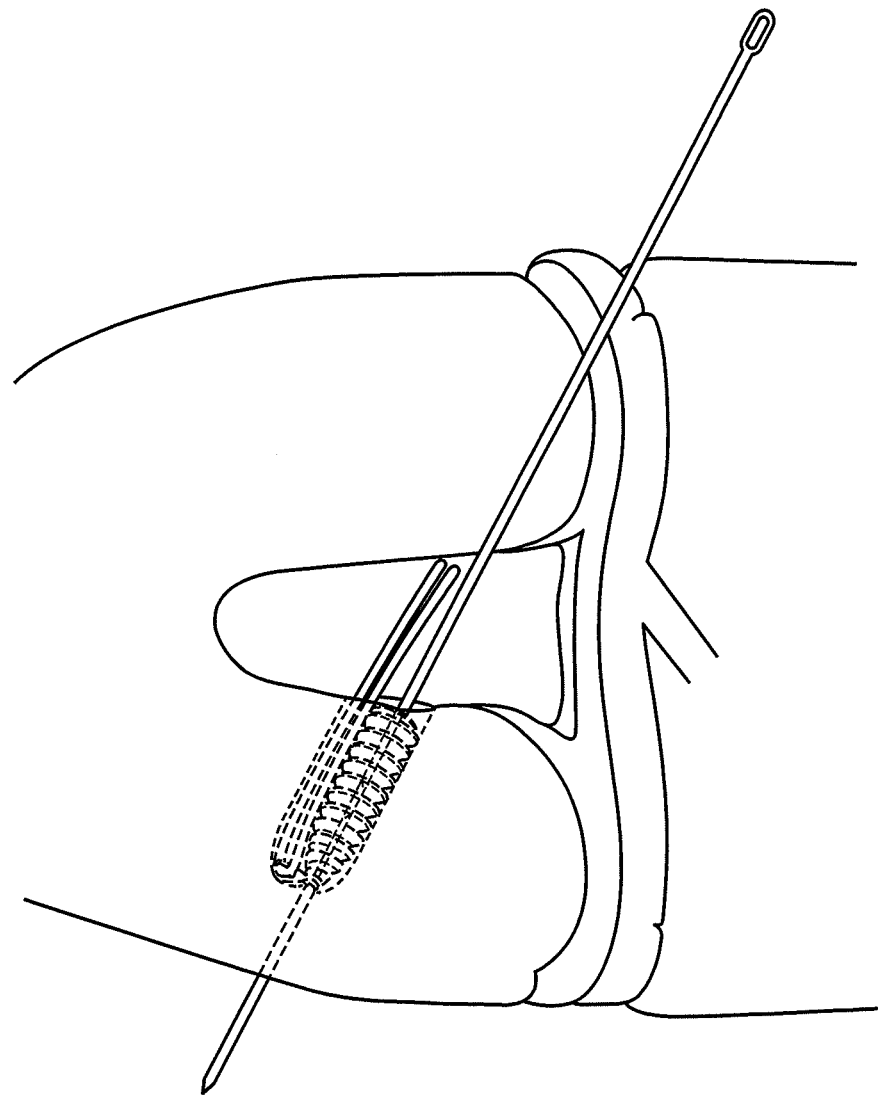

FIG. 3G illustrates the insertion of the knotless screw over the guide wire/pin into the pre drilled hole within the lateral femoral notch; the graft is inserted into the adjacent channel. The anchor and graft may be pushed or pulled (using the guidewire) into position. For example, a pusher may be used to drive the anchor into the channel drilled in the bone. In some variations the anchor is screwed into the channel, over the guidewire; for example an applicator may removably couple with the proximal end of the anchor and allow it to be inserted into the femur by pushing and/or screwing, particularly in the threaded screw-type anchors. The graft, which is coupled to the distal end of the anchor, may stay in the adjacent channel as the anchor is inserted; the coupling region for the scaffold/graft is rotatable relative to the rest of the anchor, thus as the anchor is rotated to insert, the graft may stay in the channel. As shown in FIG. 3H, the reinforcement graft sits snuggly within the pre-punched tunnel just superior to the anchor, allowing optimal in-growth of the graft into the femoral bone.

Figure 4A:
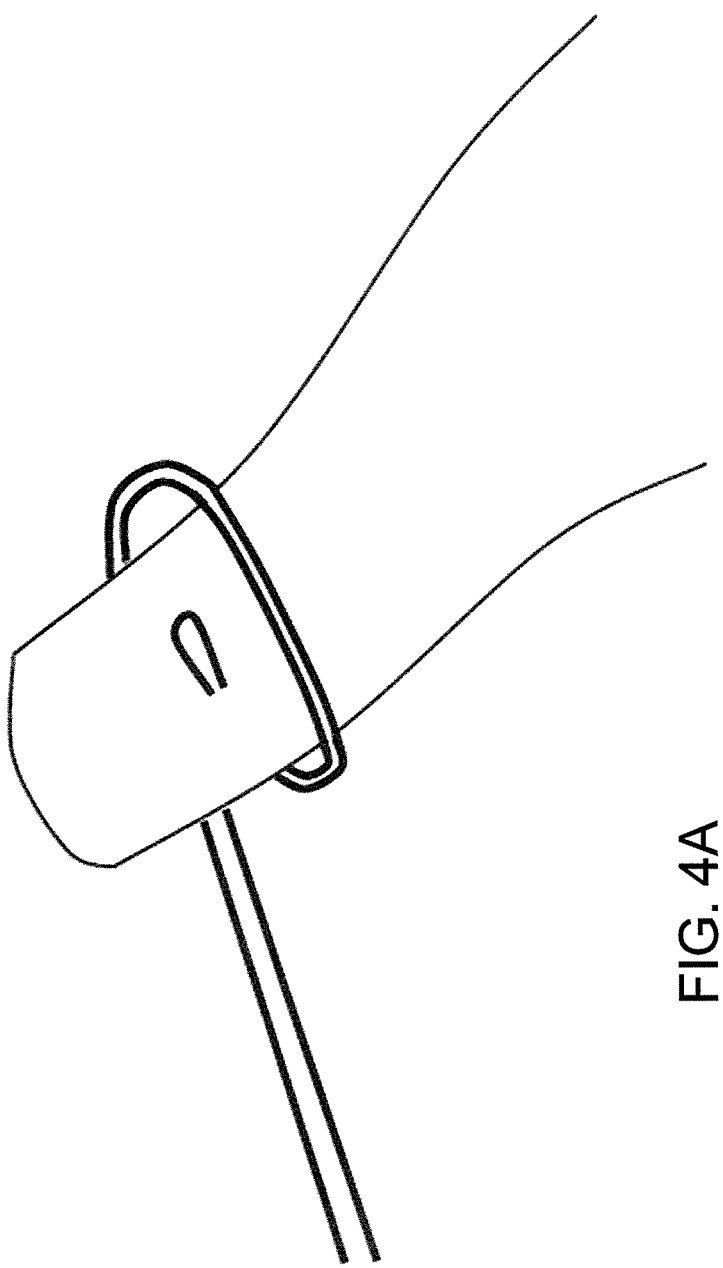
FIGS. 4A-4D illustrate one method of securing an ACL (e.g., a torn ACL) to a suture as described herein.
Figure 4B:
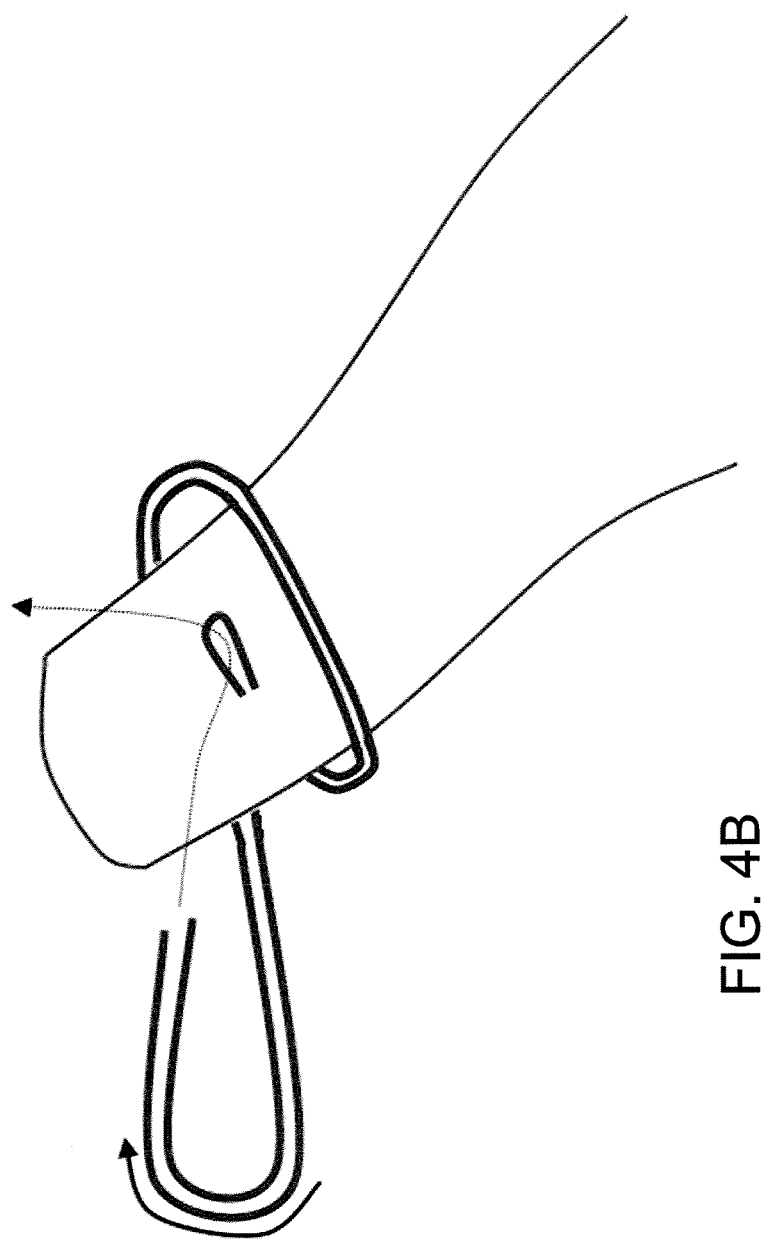
Figure 4C:
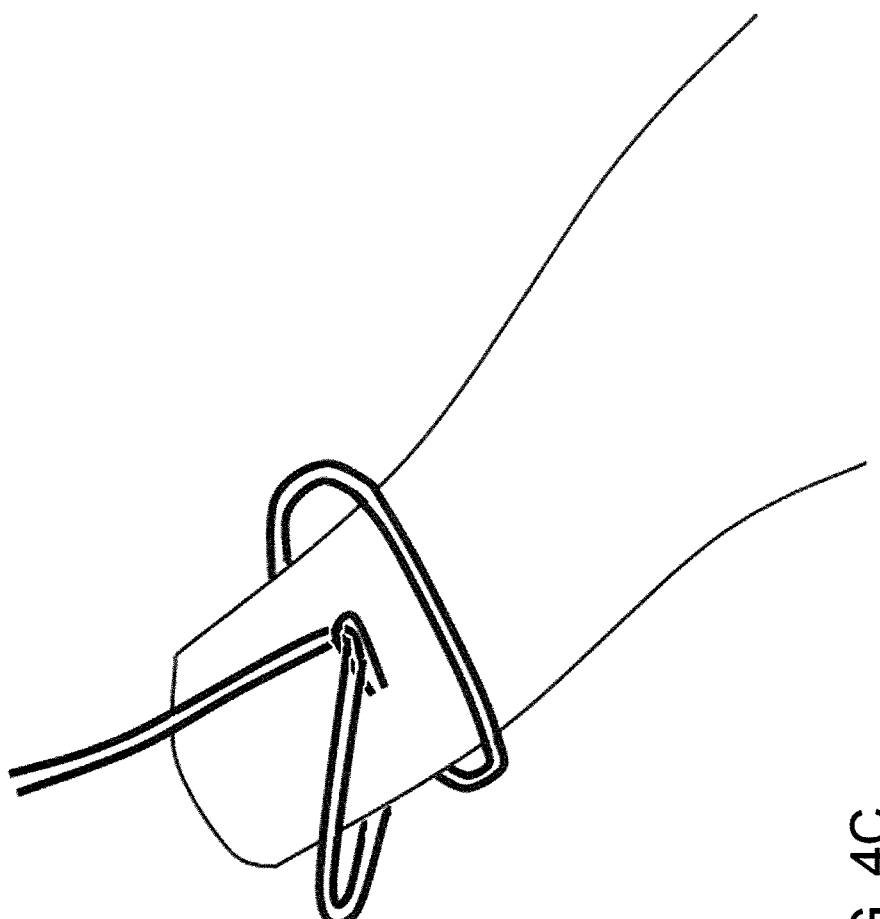
Figure 4D:
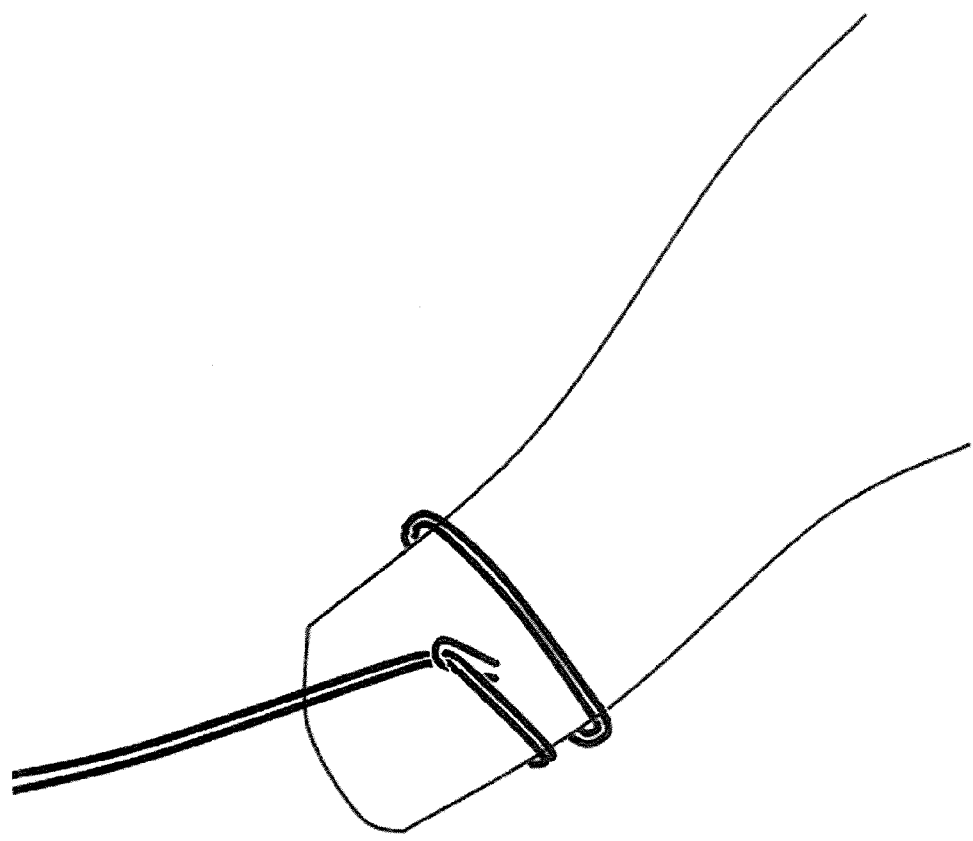
Figure 5:
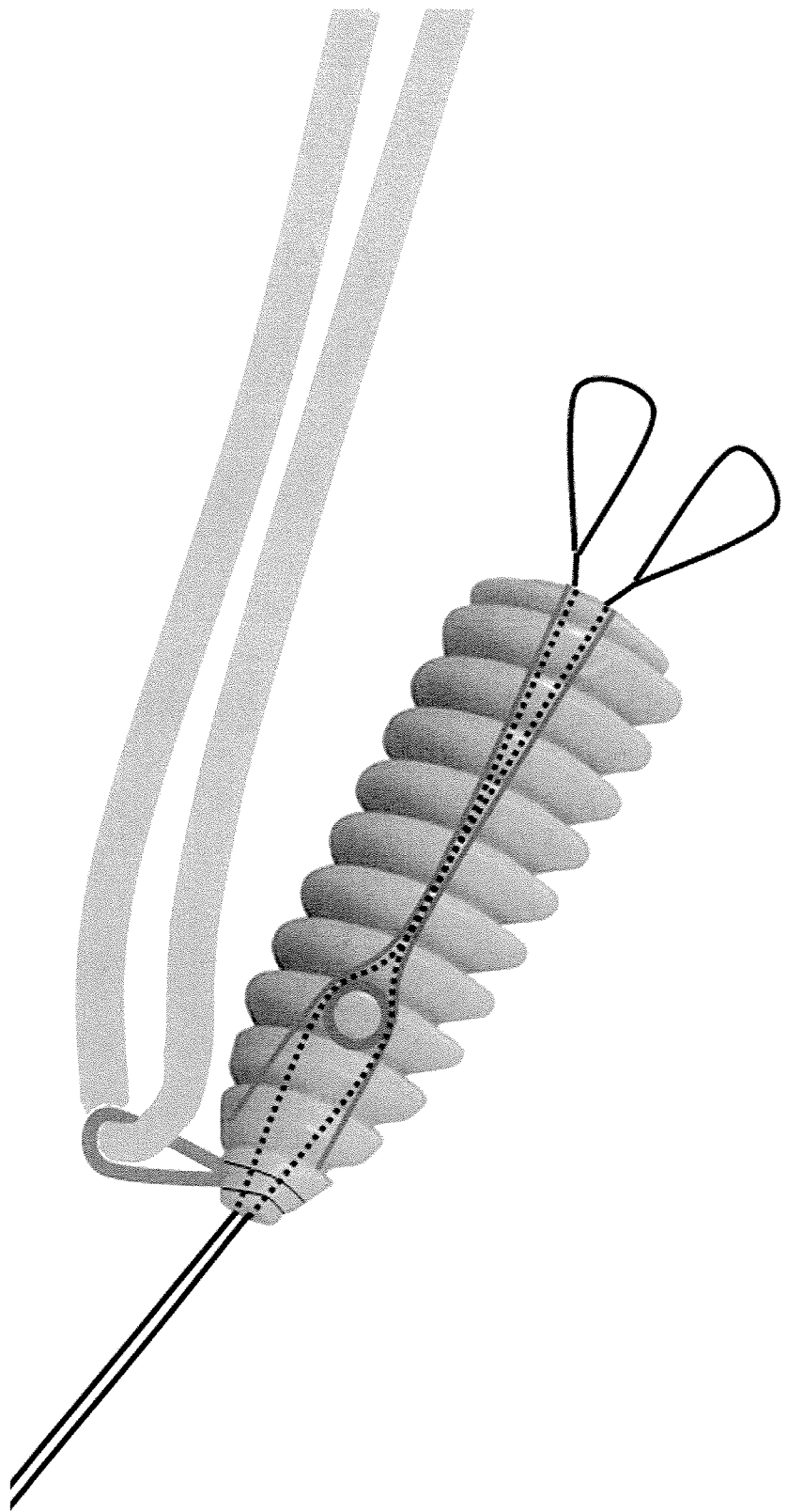
FIG. 5 shows another variation of a knotless ACL repair screw.

Once the anchor is secured in the femoral arch with the graft extending from the arch, the end region of the ACL may be pulled into position using a suture. Prior to this step the ACL may be secured with a suture as shown in FIGS. 4A-4D. In FIG. 4A, the ACL is sutured to securely attach the end of the ACL to a doubled-back suture. In this example a continuous suture passer may be used to pass the midpoint of a free suture around and then through the ACL stump, as shown in FIG. 4A. In FIG. 4B, the suture is then fed through the loop to secure the tissue in a self cinching manner, as shown in FIG. 4C. In some variations, this can be done outside of the knee, without tissue interference, because the suture has been inserted into the knee, passed through the ACL tissue, and removed all through the same single pathway. Finally as shown in FIG. 4D, the ligament is now secured and the sutures are ready to be loaded into the knotless anchor.

Figure 3I:
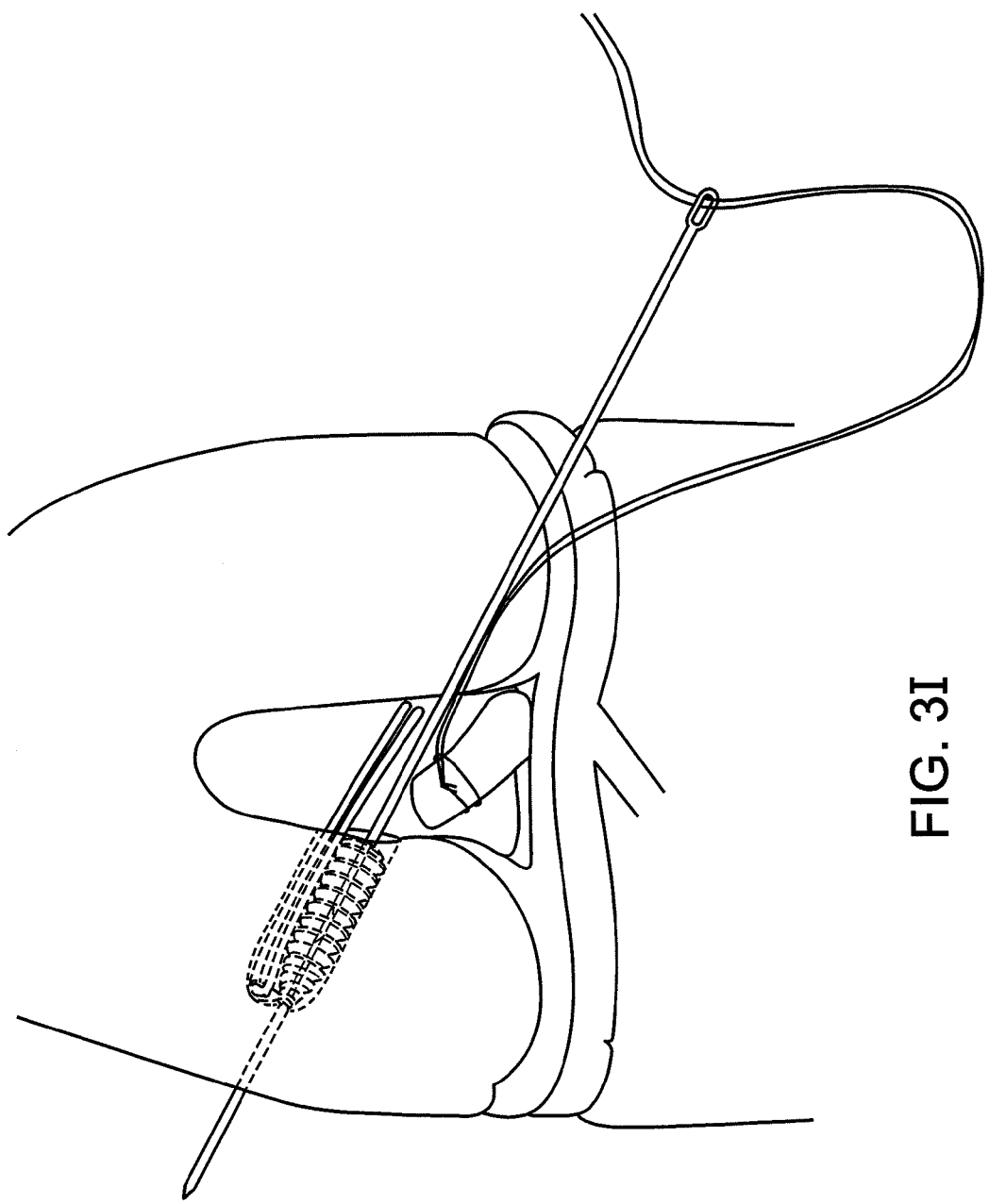
Figure 3J:
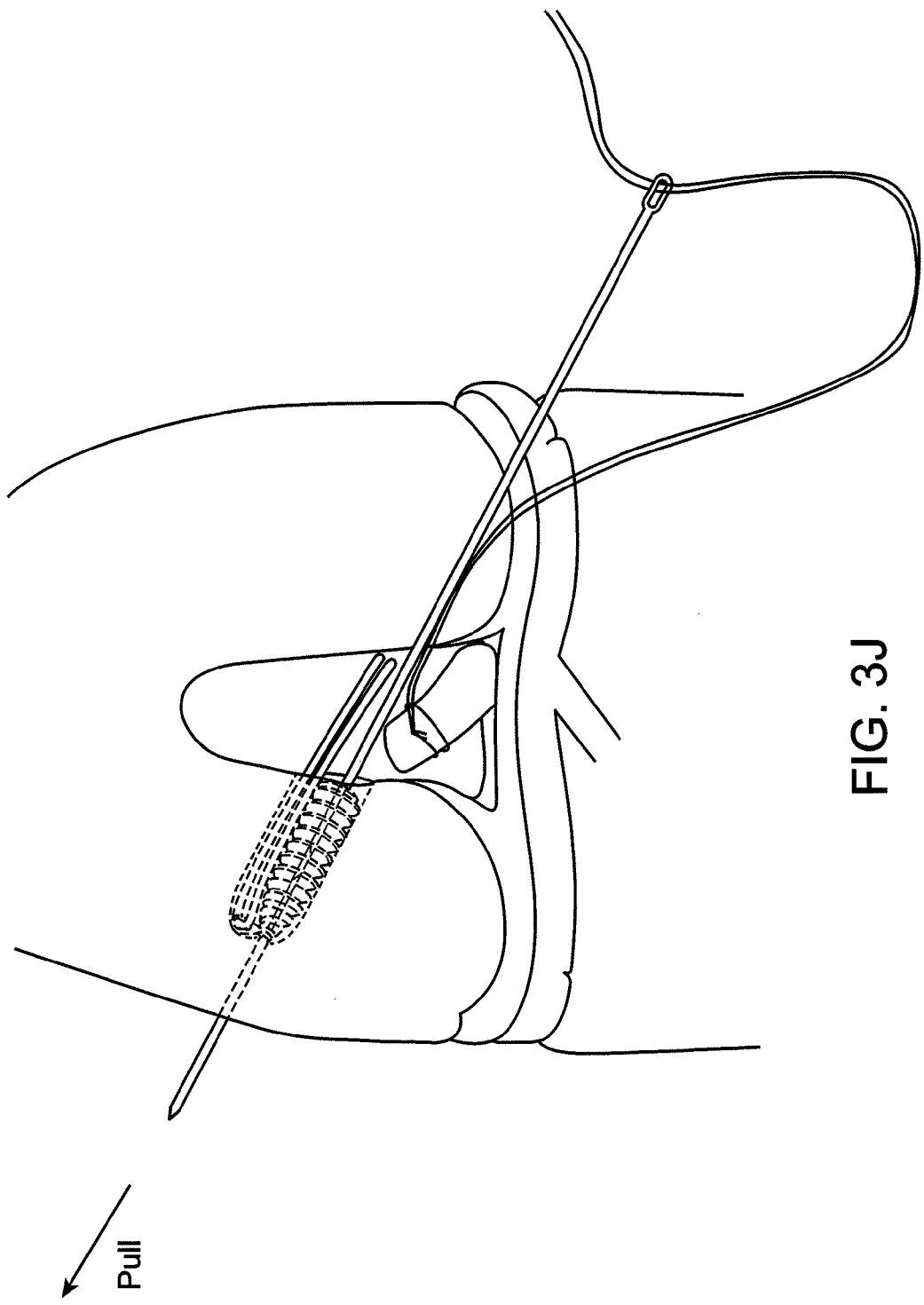
Figure 3K:
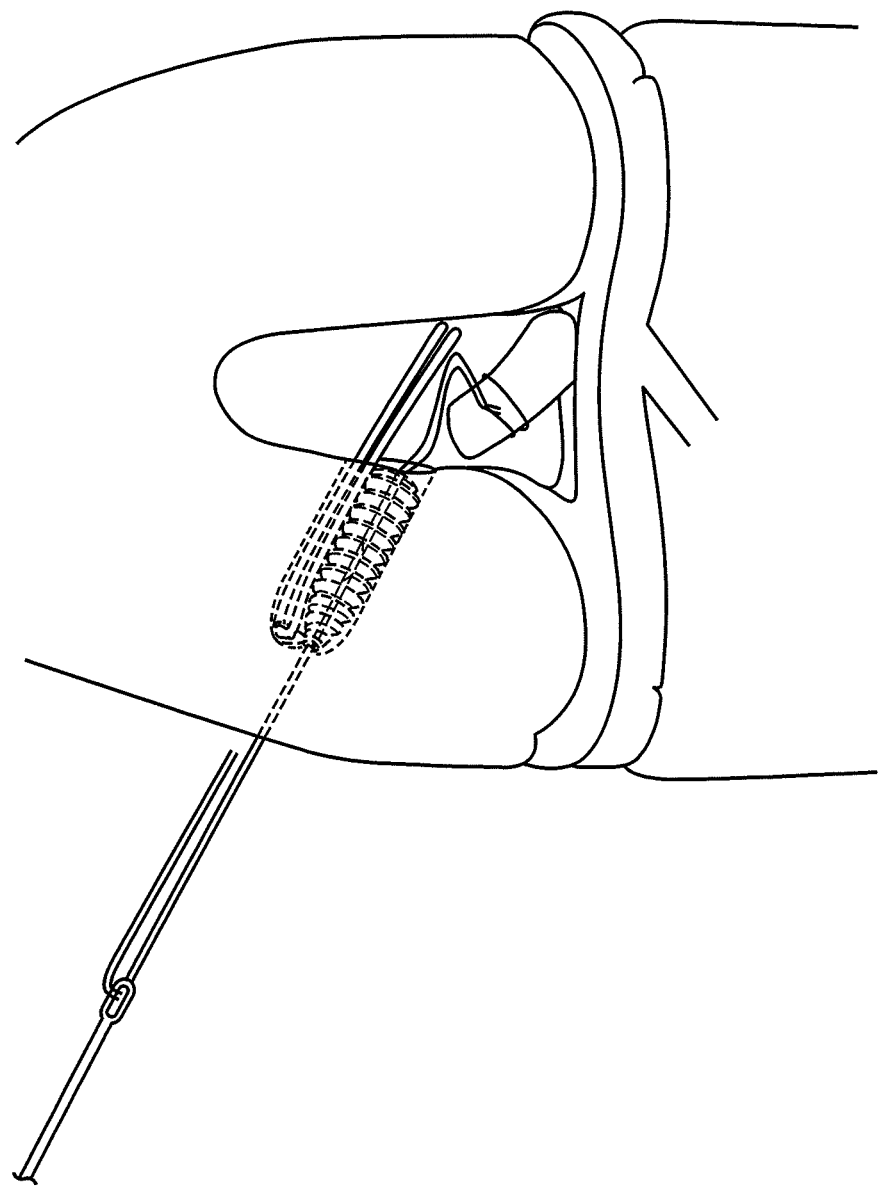
Figure 3L:
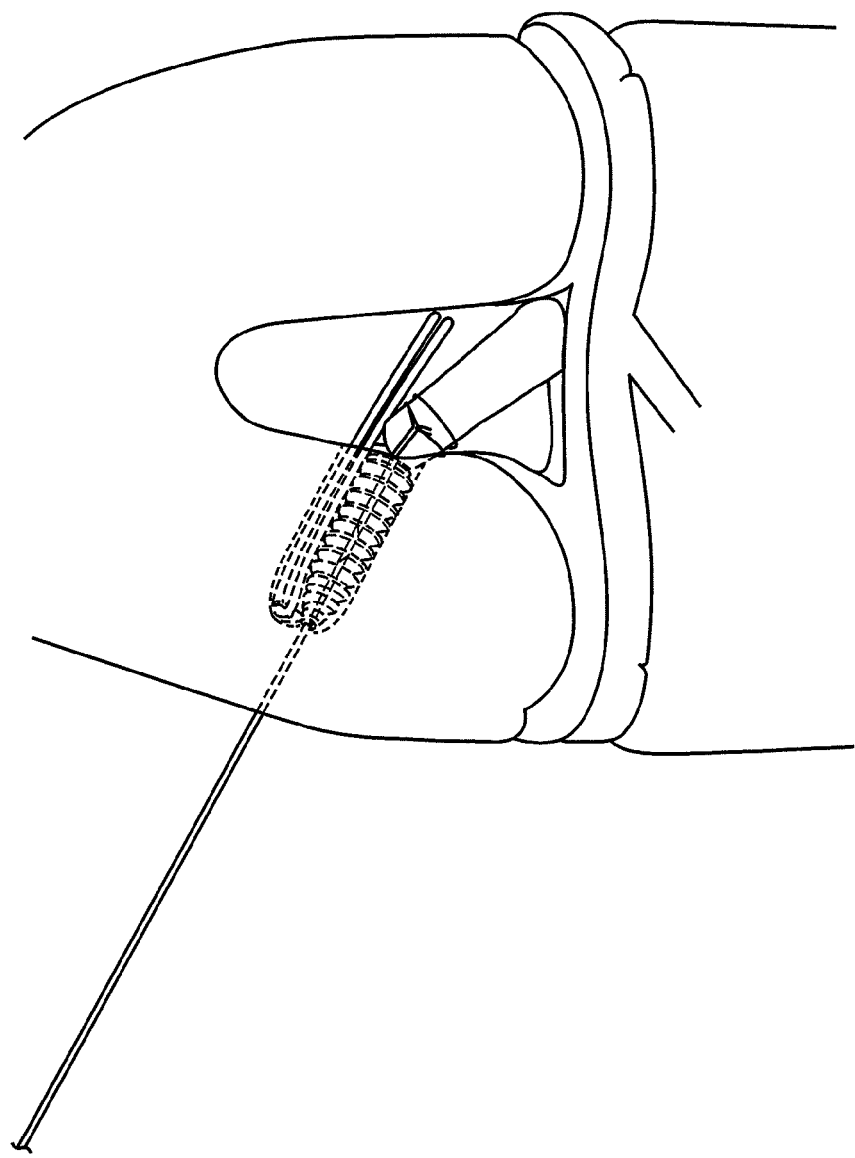

Returning now to FIG. 3I, the suture ends from the previously sewn ACL may then be fed into the eyelet of the beath pin (which may be done outside of the knee), and the beath pin drawn through the anchor (e.g., pulling distally and/or pushing proximally) to draw the ACL to the proximal end of the anchor and adjacent to the graft, as shown in FIG. 3J. For example, the beath pin may then be pulled out from the lateral knee as is typically done with current ACL reconstruction techniques, and the suture follows and is therefore loaded into the anchor. In FIG. 3K, both ends of the suture have been withdrawn through the anchor distally by pulling on beath pin (guidewire) as illustrated. Because the suture channel through the guidewire does not allow the suture(s) to be withdrawn proximally, either or both ends of the suture may be pulled distally to draw the end of the ACL near the proximal end of the anchor within the bone, and adjacent to the graft.

Figure 3M:
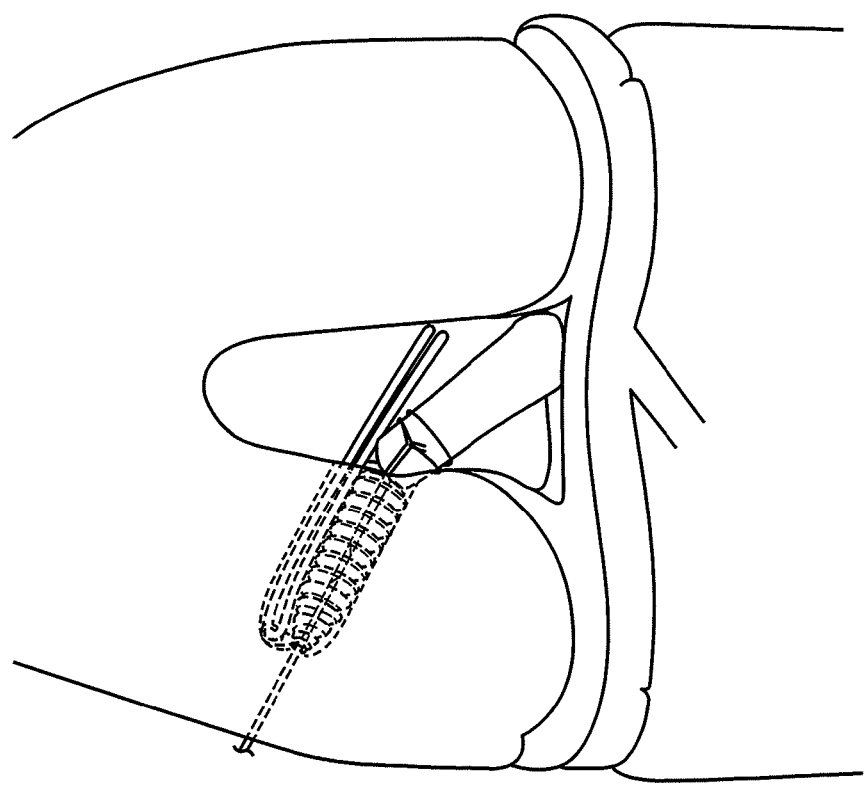

The ligament can be tensioned by pulling on the sutures with the desired amount of force. This may reduce the knee (e.g., pulling the tibia back into position relative to the femur) and may bring the ACL tissue back to its origin on the femoral notch. Thereafter the proximal end of the suture may be knotted and cut, as shown in FIG. 3M. For example, a small (e.g., 2 mm) incision can be made where the sutures exit the skin and any standard arthroscopic knot cutter can be slid down to the lateral femur where the sutures can then be safely cut flush with the bone.

Figure 3N:
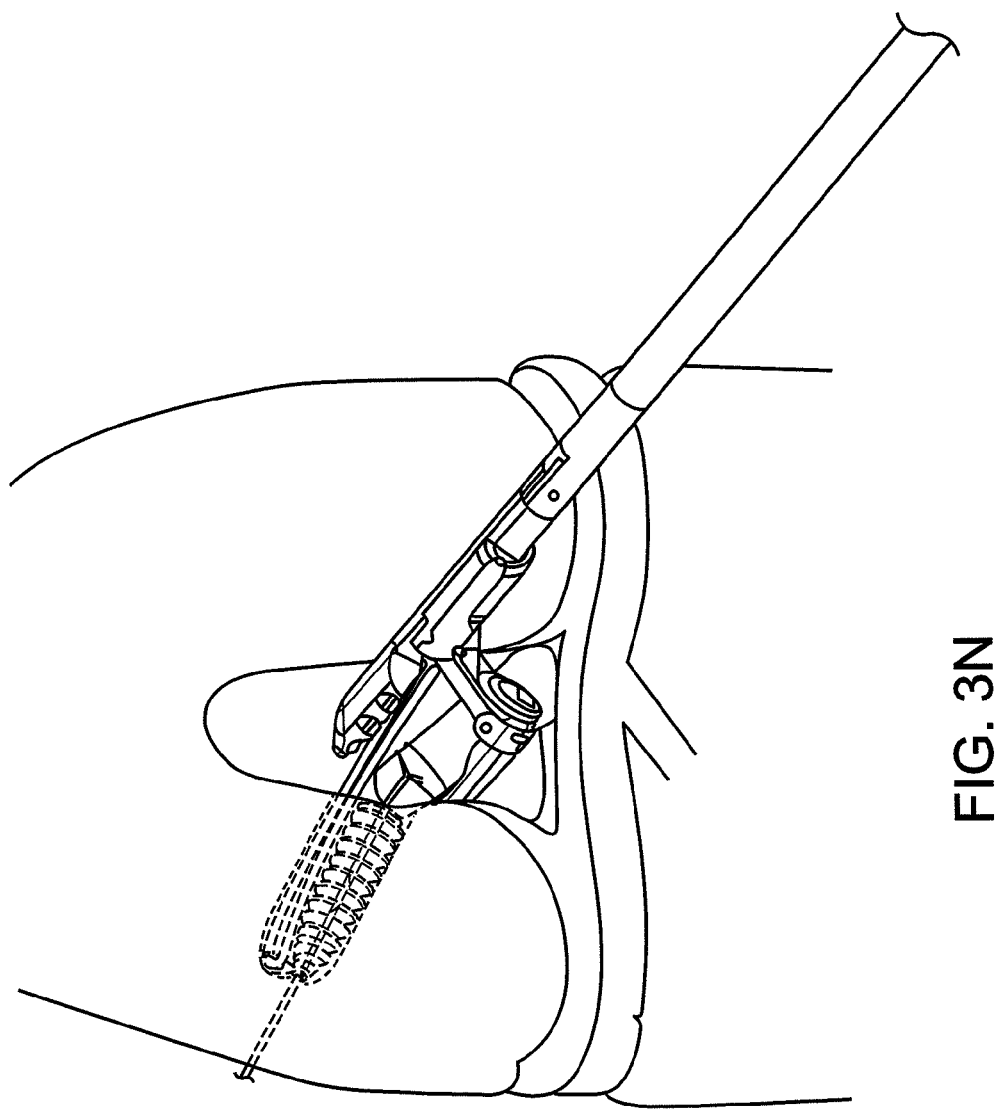
Figure 30:
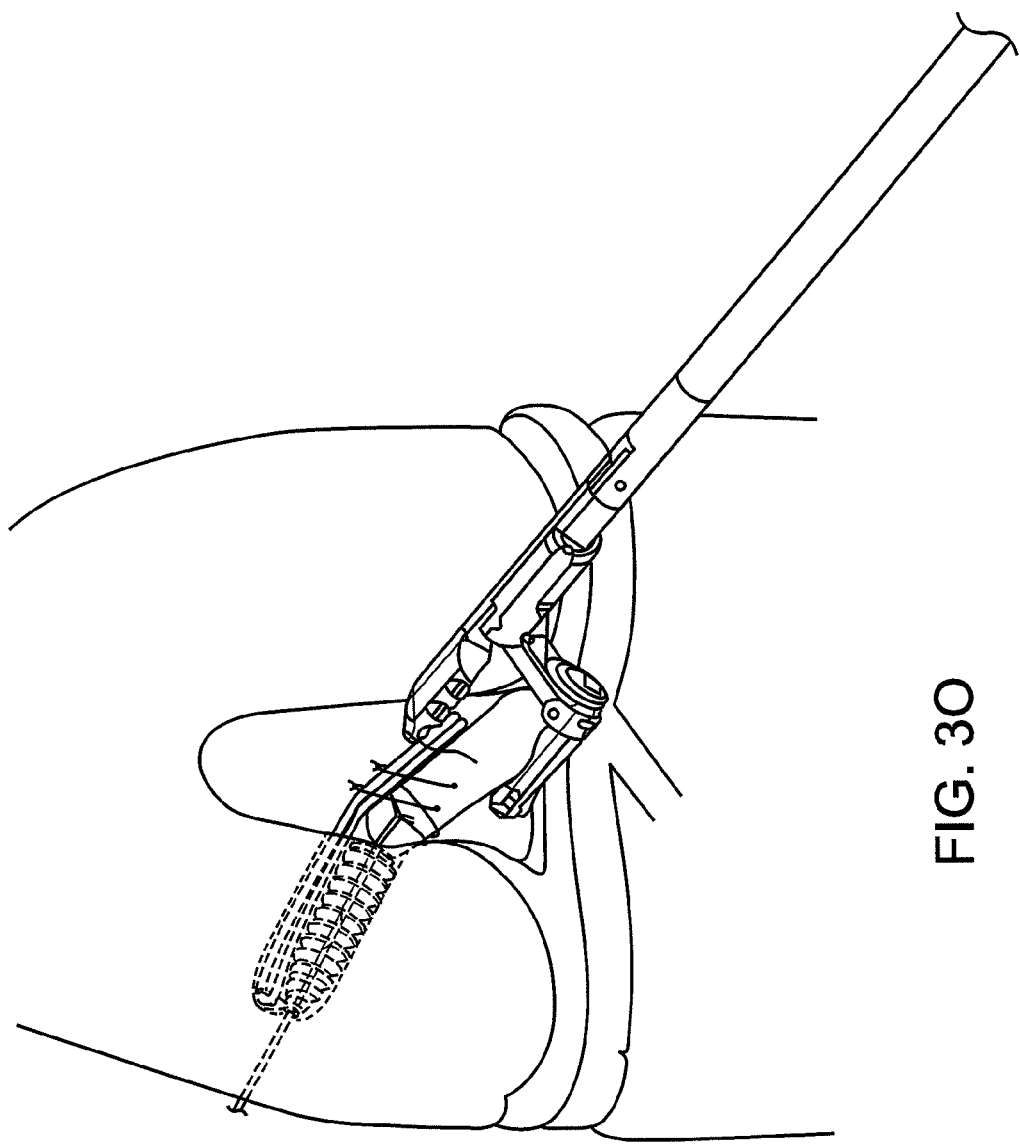
Figure 3P:
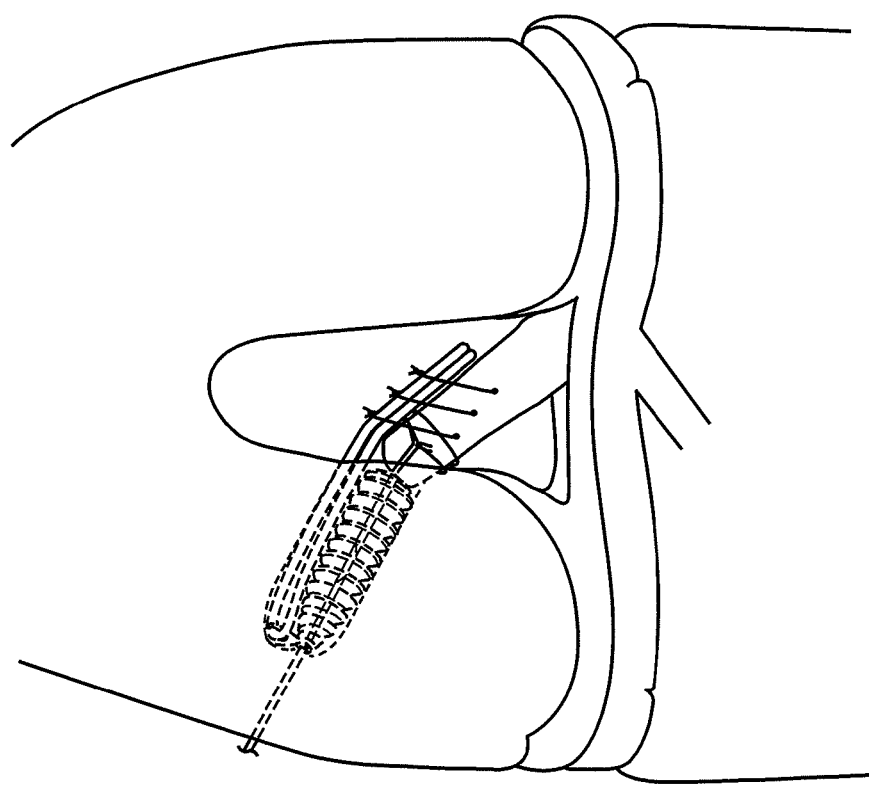

Finally, the ACL can be sutured to the graft/support material, as shown in FIGS. 3N to 3P. In this example, the continuous suture passer is brought in to sew the graft to the ACL to reinforce the repair. The continuous suture passers described herein may be positioned within the notch and still function to pass a suture through the ACL and the graft material, within the limited space of the notch. The final repair allows for a well-tensioned, significantly reinforced ACL repair.

In some variations, platelet-rich plasma or other biologic healing stimulants may also be added following or during the procedure in the notch. Note that FIGS. 3A-3P are not drawn to scale. For illustrative purposes, the screw anchor shown in the figures appears larger than the ligament in the drawings; in actuality the ligament is likely to be considerably larger that the screw.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for repairing a torn anterior cruciate ligament (ACL) within the femoral notch, the method comprising:
    forming a tunnel through a femur extending from a first side of the femur to a second side of the femur that is within the femoral notch;
    anchoring a graft within the femoral notch by securing a suture anchor coupled to the graft within the tunnel near the second side of the femur;
    securing a torn end of the ACL to a suture; and
    anchoring the suture in the suture anchor by pulling the suture through the anchor from the second side of the femur and out of the first side of the femur, wherein the anchor is configured to prevent the suture from pulling out of the anchor toward the second side of the femur; and suturing a torn end of the ACL to the graft within the femoral notch.

2. A method for repairing a torn anterior cruciate ligament (ACL) within the femoral notch, the method comprising:

forming a tunnel through a femur extending from a first side of the femur to a second side of the femur that is within the femoral notch;

securing a suture anchor within the tunnel near the second side of the femur;

securing a torn end of the ACL to a suture; and anchoring the suture in the suture anchor by pulling the suture through the anchor from the second side of the femur and out of the first side of the femur, wherein the anchor is configured to prevent the suture from pulling out of the anchor toward the second side of the femur.

3. The method of claim 2, wherein forming the tunnel comprises driving a pin through the femur.

4. The method of claim 2, further comprising securing the ACL to a graft connected to the suture anchor.

5. The method of claim 2, wherein securing the torn end of the ACL comprises pulling the suture through the tunnel and anchor to position the torn end of the ACL adjacent to a graft and suturing the torn end of the ACL to the graft.

6. The method of claim 2, wherein securing a suture anchor comprises securing the anchor to which a graft has been coupled within the femur so that a proximal end of the graft extends from the second side of the femur.

7. The method of claim 2, wherein forming a tunnel through a femur comprises driving a guidewire through the femur and drilling an opening to hold the suture anchor.

8. The method of claim 2, wherein the suture anchor is secured by screwing the anchor into the femur.

9. The method of claim 2, wherein suturing the torn end of the ACL comprises passing the suture through the ACL multiple times with a continuous suture passer without removing the suture passer from the tissue.

10. The method of claim 2, further comprising tensioning the ACL by pulling the suture from the first side of the femur.

11. The method of claim 2, further comprising knotting and securing the suture from the first side of the femur.

12. A method for repairing a torn ligament within the femoral notch, the method comprising:

forming a tunnel through a femur extending from a first side of the femur facing away from the femoral notch to a second side of the femur that is within the femoral notch;

securing a suture anchor within the tunnel near the second side of the femur;

percutaneously securing a torn end of the ligament to a suture using a suture passer from within the femoral notch; and pulling the suture through the anchor from the second side of the femur and out of the first side of the femur, wherein the anchor is configured to prevent the suture from pulling out of the anchor toward the second side of the femur.

13. The method of claim 12, further comprising securing the ligament to a graft connected to the suture anchor.

14. The method of claim 12, wherein securing the torn end of the ligament comprises pulling the suture through the tunnel and anchor to position the torn end of the ligament adjacent to a graft and suturing the torn end of the ligament to the graft.

15. The method of claim 12, wherein securing a suture anchor comprises securing the anchor to which a graft has been coupled within the femur so that a proximal end of the graft extends from the second side of the femur.

16. The method of claim 12, wherein forming a tunnel through a femur comprises driving a guidewire through the femur and drilling an opening to hold the suture anchor.

17. The method of claim 12, wherein the suture anchor is secured by screwing the anchor into the femur.

18. The method of claim 12, wherein suturing the torn end of the ligament comprises passing the suture through the ligament multiple times with a continuous suture passer without removing the suture passer from the tissue.

19. The method of claim 12, further comprising tensioning the ligament by pulling the suture from the first side of the femur.

20. The method of claim 12, further comprising knotting and securing the suture from the first side of the femur.

* * * * *